(12) United States Patent
Lih et al.

(10) Patent No.: US 8,691,780 B2
(45) Date of Patent: Apr. 8, 2014

(54) TXR1 AND ENHANCED TAXANE SENSITIVITY BASED ON THE MODULATION OF A PATHWAY MEDIATED THEREBY

(75) Inventors: Chih Jian Lih, Palo Alto, CA (US); Stanley N. Cohen, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1267 days.

(21) Appl. No.: 11/357,728

(22) Filed: Feb. 16, 2006

(65) Prior Publication Data

US 2007/0209082 A1    Sep. 6, 2007

Related U.S. Application Data

(60) Provisional application No. 60/654,343, filed on Feb. 17, 2005.

(51) Int. Cl.
   - *C12N 15/11*    (2006.01)
   - *A61K 31/337*   (2006.01)
   - *A61K 31/341*   (2006.01)

(52) U.S. Cl.
   USPC .......... 514/44 A; 514/337; 514/444; 514/449; 514/471

(58) Field of Classification Search
   None
   See application file for complete search history.

(56) References Cited

U.S. PATENT DOCUMENTS

| | | | |
|---|---|---|---|
| 5,200,534 A | 4/1993 | Rao | |
| 5,202,448 A | 4/1993 | Carver et al. | |
| 5,229,529 A | 7/1993 | Ueno et al. | |
| 5,274,137 A | 12/1993 | Nicolaou et al. | |
| 5,279,949 A | 1/1994 | Nair | |
| 5,283,253 A | 2/1994 | Holton et al. | |
| 5,294,637 A | 3/1994 | Chen et al. | |
| 5,415,869 A * | 5/1995 | Straubinger et al. | 424/450 |
| 5,821,263 A | 10/1998 | Scola et al. | |
| 5,824,701 A | 10/1998 | Greenwald et al. | |
| 5,869,680 A | 2/1999 | Mas et al. | |
| 6,380,161 B1 * | 4/2002 | Williams et al. | 514/12 |
| 6,524,583 B1 | 2/2003 | Thorpe et al. | |
| 2003/0065151 A1 * | 4/2003 | Ruben et al. | 530/388.26 |
| 2004/0005563 A1 * | 1/2004 | Mack et al. | 435/6 |
| 2004/0127441 A1 * | 7/2004 | Gleave et al. | 514/44 |
| 2006/0240002 A1 | 10/2006 | Brooks et al. | |

FOREIGN PATENT DOCUMENTS

| | | |
|---|---|---|
| EP | 0590 267 A2 | 4/1994 |
| WO | WO 93/10076 | 5/1993 |
| WO | WO 93/23555 | 11/1993 |
| WO | WO 94/07876 | 4/1994 |
| WO | WO 94/07880 | 4/1994 |
| WO | WO 94/07881 | 4/1994 |
| WO | WO 94/07882 | 4/1994 |
| WO | WO 98/13059 | 4/1998 |
| WO | WO 98/28288 | 7/1998 |
| WO | WO 98/58927 | 12/1998 |
| WO | WO 99/09021 | 2/1999 |
| WO | WO 99/18113 | 4/1999 |
| WO | WO 02/078606 A2 * | 10/2002 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Burgess et al., J of Cell Bio. 111:2129-2138, 1990.*
Lazar et al. Molecular and Cellular Biology 8:1247-1252, 1988.*
(Bowie et al. Science, 247:1306-1310, 1990.*
Manna et al. (Cancer Research,Feb. 1, 2004, 64: 1026-1036).*
Kanada et al. (Exp. Cell Res. 1999, 252: 262-272).*
Tannock, I.F. (Experimental Chemotherapy, Ch. 19—p. 338 and 352-359, in The Basic Science of Oncology Tannock and Hill, eds., New York 1992).*
Sobell, H. M. (Proc. Natl. Acad. Sci. Aug. 1985 82:5328-5331).*
Lin CH et al TXrl: a transcriptional regulator of thrombospondin-1 that modulates cellular sensitivity to taxanes. Genes Dev. Aug. 1, 2006; 2082-95.
Van Amerongen R et al TXR1-mediated thrombospondin repression: a novel mechanism of resistance to taxanes? Genes Dev. Aug. 1, 2006; 20 (15): 1975-81.
Zhang et al Thrombospondin-based antiangiogentic therapy. Microwasc Res. Sep.-Nov. 2007; 74 (2-3): 90-9.

* cited by examiner

*Primary Examiner* — Peter J Reddig
(74) *Attorney, Agent, or Firm* — Bozicevic, Field & Francis LLP; Bret E. Field; Kyle A. Gurley

(57) ABSTRACT

Methods and compositions for enhancing taxane sensitivity are provided. Aspects of the subject methods include administering to a subject a txr1 pathway modulatory agent in conjunction with a taxane. Also provided are txr1 polypeptides and nucleic acids encoding the same. The subject methods and compositions find use in a variety of different applications.

12 Claims, 7 Drawing Sheets

Fig 1.
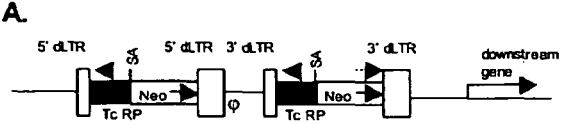
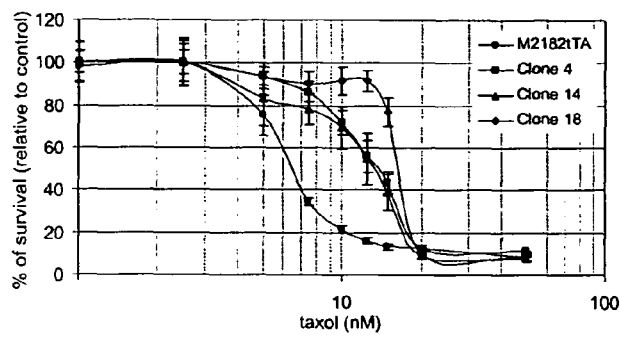
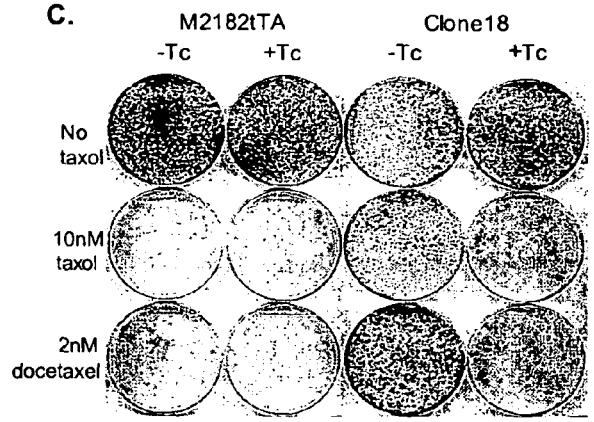
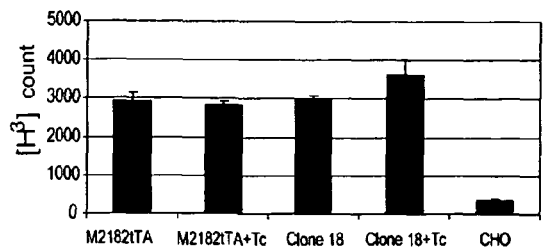
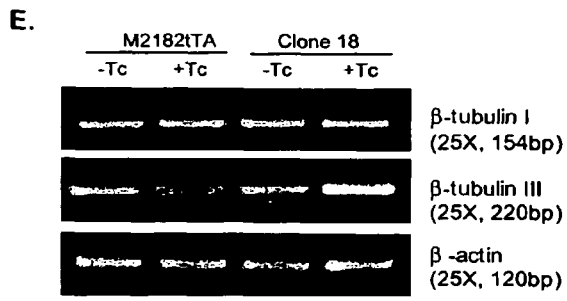

Fig. 4
A.
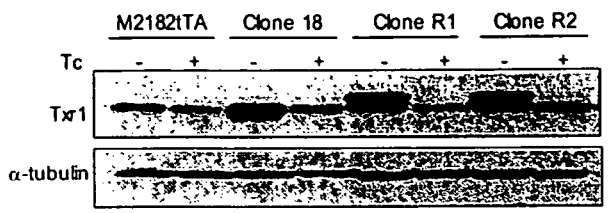
B.
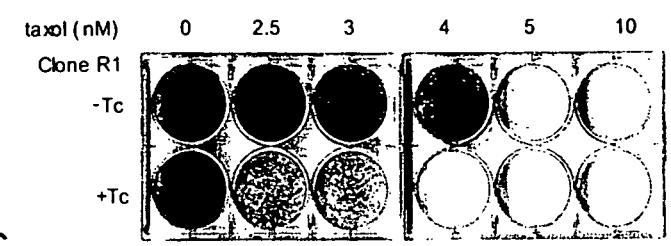
C.
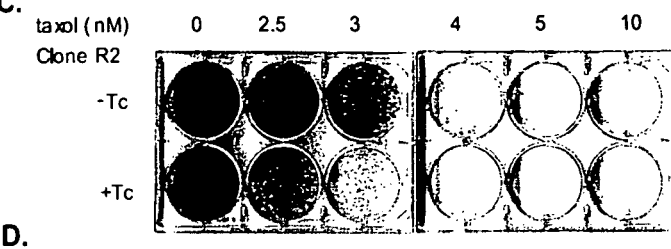
D.
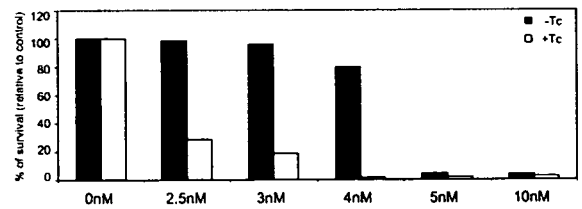
E.
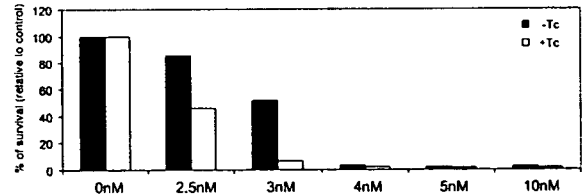

Fig. 6
A.
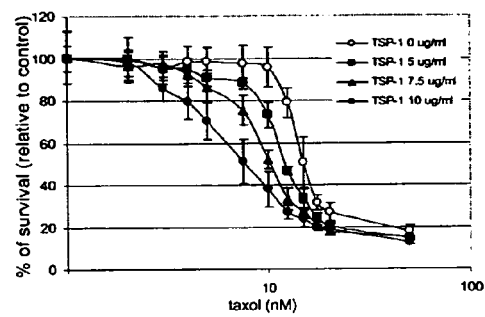
C.
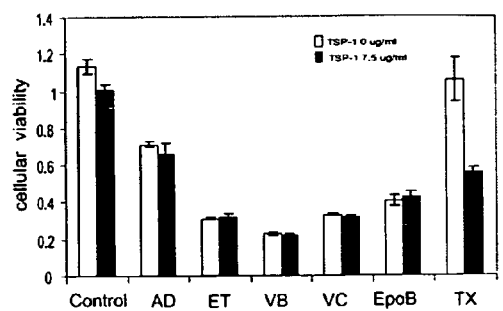
B.
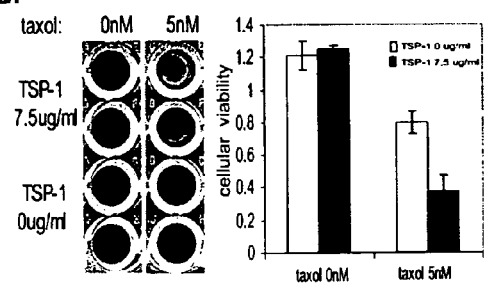
D.
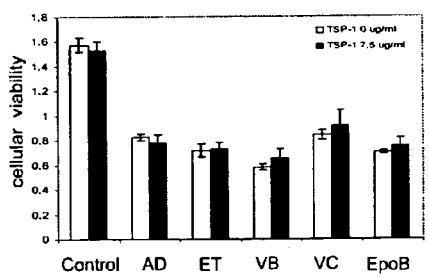
E.
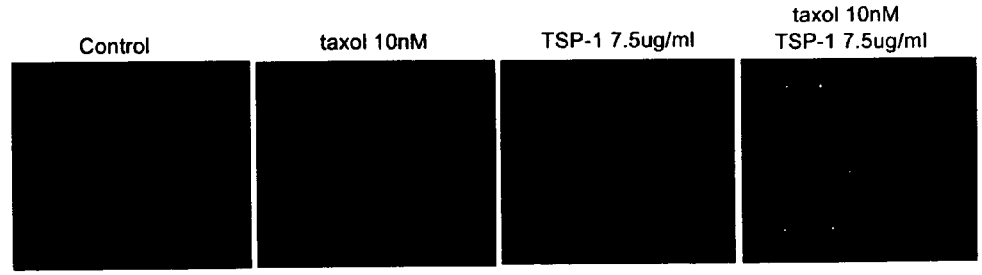
F.
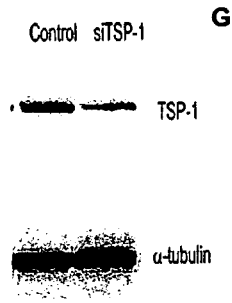
G.
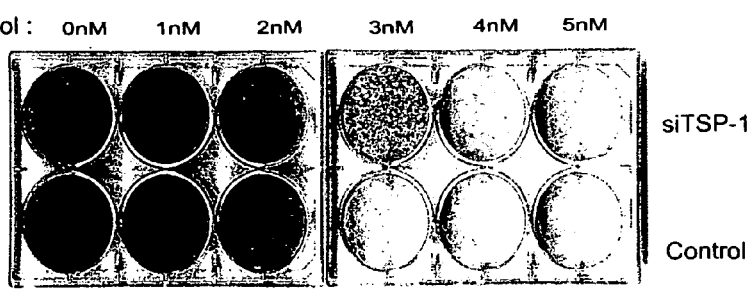

Fig 7.
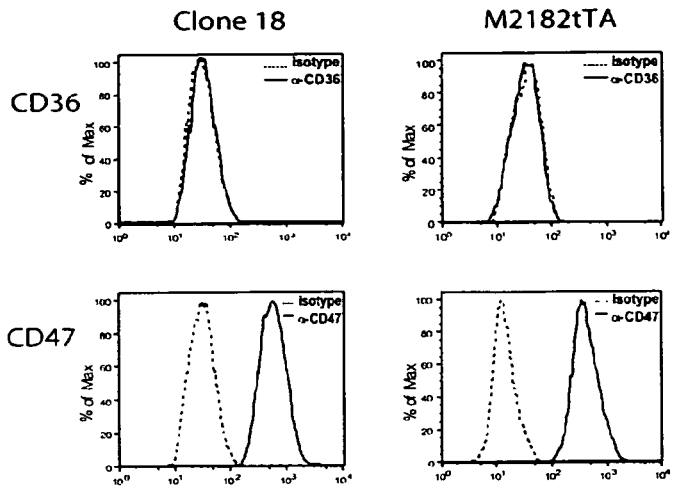
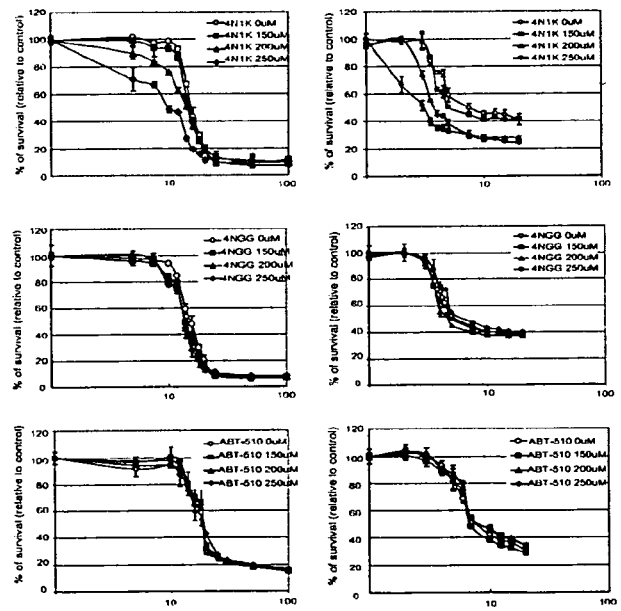
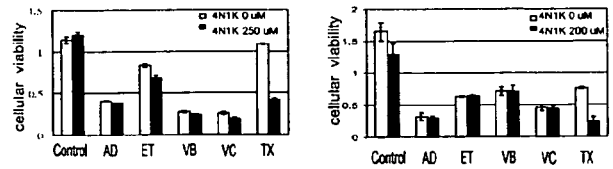
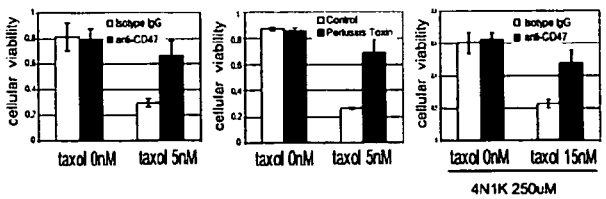

SEQUENCE LISTING

```
<160> NUMBER OF SEQ ID NOS: 16

<210> SEQ ID NO 1
<211> LENGTH: 10
<212> TYPE: PRT
<213> ORGANISM: human

<400> SEQUENCE: 1

Lys Arg Phe Tyr Val Val Met Trp Lys Lys
 1               5                  10

<210> SEQ ID NO 2
<211> LENGTH: 10
<212> TYPE: PRT
<213> ORGANISM: human
```

```
<400> SEQUENCE: 2

Lys Arg Phe Tyr Gly Gly Met Trp Lys Lys
  1               5                  10

<210> SEQ ID NO 3
<211> LENGTH: 7
<212> TYPE: PRT
<213> ORGANISM: human

<400> SEQUENCE: 3

Gly Val Ile Thr Arg Ile Arg
  1               5

<210> SEQ ID NO 4
<211> LENGTH: 26
<212> TYPE: DNA
<213> ORGANISM: bacteria

<400> SEQUENCE: 4
gctgaccgct tcctcgtgct ttacgg                                      26

<210> SEQ ID NO 5
<211> LENGTH: 20
<212> TYPE: DNA
<213> ORGANISM: human

<400> SEQUENCE: 5
acctcgctgc tccagcctct                                             20

<210> SEQ ID NO 6
<211> LENGTH: 20
<212> TYPE: DNA
<213> ORGANISM: human

<400> SEQUENCE: 6
ccggcctgga tgtgcacgat                                             20

<210> SEQ ID NO 7
<211> LENGTH: 27
<212> TYPE: DNA
<213> ORGANISM: human

<400> SEQUENCE: 7
acatctcttc aggcctgaca atttcat                                     27

<210> SEQ ID NO 8
<211> LENGTH: 30
<212> TYPE: DNA
<213> ORGANISM: human

<400> SEQUENCE: 8
tgctgatgag caacgtgccc atgccggagc                                  30

<210> SEQ ID NO 9
<211> LENGTH: 21
<212> TYPE: DNA
<213> ORGANISM: human

<400> SEQUENCE: 9
atggttggac cagcagtgat a                                           21

<210> SEQ ID NO 10
<211> LENGTH: 21
```

```
<212> TYPE: DNA
<213> ORGANISM: human

<400> SEQUENCE: 10
ggaagggtcc agggcctgta t                                              21

<210> SEQ ID NO 11
<211> LENGTH: 15
<212> TYPE: PRT
<213> ORGANISM: human

<400> SEQUENCE: 11

Ala Gly Gln Pro Gly Pro Asn Pro Tyr Pro Pro Asn Ile Gly Cys
 1               5                  10                  15

<210> SEQ ID NO 12
<211> LENGTH: 22
<212> TYPE: RNA
<213> ORGANISM: human

<400> SEQUENCE: 12
aagagcgaga cugcgaagga ga                                             22

<210> SEQ ID NO 13
<211> LENGTH: 21
<212> TYPE: RNA
<213> ORGANISM: human

<400> SEQUENCE: 13
ucuccuucgc agucucggcu c                                              21

<210> SEQ ID NO 14
<211> LENGTH: 23
<212> TYPE: RNA
<213> ORGANISM: human

<400> SEQUENCE: 14
aagaggauug ccauggccug gcc                                            23

<210> SEQ ID NO 15
<211> LENGTH: 21
<212> TYPE: RNA
<213> ORGANISM: human

<400> SEQUENCE: 15
ggccaggcca uggcaauccu c                                              21

<210> SEQ ID NO 16
<211> LENGTH: 148
<212> TYPE: PRT
<213> ORGANISM: human

<400> SEQUENCE: 16

Met Trp Asn Pro Asn Ala Gly Gln Pro Gly Pro Asn Pro Tyr Pro Pro
 1               5                  10                  15

Asn Ile Gly Cys Pro Gly Gly Ser Asn Pro Ala His Pro Pro Pro Ile
             20                  25                  30

Asn Pro Pro Phe Pro Pro Gly Pro Cys Pro Pro Pro Gly Ala Pro
         35                  40                  45

His Gly Asn Pro Ala Phe Pro Pro Gly Gly Pro His Pro Val Pro
     50                  55                  60

Gln Pro Gly Tyr Pro Gly Cys Gln Pro Leu Gly Pro Tyr Pro Pro Pro
65                  70                  75                  80
```

```
Tyr Pro Pro Pro Ala Pro Gly Ile Pro Pro Val Asn Pro Leu Ala Pro
            85              90                  95
Gly Met Val Gly Pro Ala Val Ile Val Asp Lys Lys Met Gln Lys Lys
            100             105             110
Met Lys Lys Ala His Lys Lys Met His Lys His Gln Lys His His Lys
        115             120              125
Tyr His Lys His Gly Lys His Ser Ser Ser Ser Ser Ser Ser Ser Ser
        130             135              140
Ser Asp Ser Asp
145
```

TXR1 AND ENHANCED TAXANE SENSITIVITY BASED ON THE MODULATION OF A PATHWAY MEDIATED THEREBY

CROSS-REFERENCE TO RELATED APPLICATIONS

Pursuant to 35 U.S.C. §119 (e), this application claims priority to the filing date of U.S. Provisional Patent Application Ser. No. 60/654,343 filed on Feb. 17, 2005; the disclosure of which application is herein incorporated by reference.

BACKGROUND

Taxane is a family of major chemotherapeutic agents that have anti-neoplastic effects against a wide spectrum of human cancers. Despite a dramatic response of susceptible tumors to initial treatment with taxanes, the subsequent development of resistance to these drugs has proved to be a major limitation to long-term use of these agents as anticancer drugs. Two well-studied mechanisms associated with such resistance are: (1) mutations in ATP dependant P-glycoproteins that lead to exclusion of taxanes and a variety of other drugs from cells (i.e. transporter-related multidrug resistance; MDR-1); and (2) mutations that affect the binding of taxanes to microtubules. However, it has long been apparent that still other undefined mechanisms are also implicated in taxane resistance.

SUMMARY

Methods and compositions for enhancing taxane sensitivity are provided. Aspects of the subject methods include administering to a subject a txr1 pathway modulatory agent in conjunction with a taxane. Also provided are txr1 polypeptides and nucleic acids encoding the same. The subject methods and compositions find use in a variety of different applications.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIGS. 1A to 1E. Identification and Characterization of Taxol Resistant Cell Clones. (FIG. 1A) Structure of integrated provirus derived from retroviral gene search vector (GSV). 3'dLTR or 5'dLTR (open boxes), designate defective retroviral long terminal repeats lacking promoter and enhancer sequences required for virion production; SA, splicing acceptor site from adenovirus; neo, reporter gene encodes resistance to G418 (arrow in box indicates the 'sense' direction of transcription; the broken arrow at the top indicates the location and 5' to 3' direction of the primer used for cloning genes adjacent to the integration site); TcRP, (filled box), tetracycline regulated promoter; the arrow head above this box indicates the direction of transcription; φ, virus packaging signal; (FIG. 1B) Survival curves of cell clones resistant to taxol. Cell clones selected from functional screening were subjected to viability analysis by MTT assay. The surviving fraction in percentage (Y-axis) for cells treated with indicated taxol concentrations (nM) (X-axis) was calculated by normalizing the MTT assay readouts to the untreated control (set as 100%). Each data point represents the mean±SD from eight replicates; (FIG. 1C) Tc effect on taxol resistance in clone 18. Equal numbers of M2182tTA and clone 18 cells were seeded and treated with the indicated concentration of taxane in the presence (+Tc) or absence (−Tc) of tetracycline (1 µg/ml) for colony forming assays. Cell colonies were stained by 0.5% crystal violet. (FIG. 1D) Tc effect on taxol uptake in clone 18. Equal numbers of the indicated cell lines were seeded, incubated with [$^3$H] taxol, washed, and subjected to scintillation counting for measuring the rate of uptake. Chinese hamster ovary (CHO) cells, which are known to contain high efflux activity were used as controls (Parekh & Simpkins, Biochem Pharmacol (1996) 51:301-311). Each histogram represents the mean±SD of four independent experiments. (FIG. 1E) Gene expression of β-tubulin isoforms. Poly(A) RNAs extracted from indicated cell lines were used as templates to quantitatively analyze expression of β-tubulins I and III by RT-PCR. The cycle number and product size are indicated.

(FIG. 2B) Txr1 protein sequence deduced from cDNA sequence (SEQ ID NO: 16). The peptide used as antigen for raising antibodies is underlined. (FIG. 2C) Effect of Tc on txr1 transcript in clone 18. Northern blot (top panel), poly(A) RNA extracted from indicated cells/conditions were fractionated by electrophoresis, transferred onto filter, and probed with radioactively labeled txr1 and β-actin cDNA fragments. The size of the txr1 transcript is indicated. The same RNAs were used as template for RT-PCR analysis (bottom panel), the cycle number and product size of the RT-PCR product are indicated. (FIG. 2D) Effect of Tc on Txr1 protein in clone 18. Cell lysates extracted from indicated cells/conditions were subjected to immunoblotting analysis and probed with anti-Txr1 and anti-α-tubulin antibodies. (FIG. 2E) Intracellular localization of Txr1. HeLa cells were immunofluorescence stained with preimmune serum (left, upper) or anti-Txr1 polyclonal antibodies (left, lower). Chinese hamster ovary cells transfected with pCMV-EGFPN1 (right, upper) or pEGFPTxr1 (right, lower) were stained with DAPI (blue). Fluorescent images were obtained by confocal microscopy. (FIG. 2F) Multiple tissue Northern blot. A filter (Clontech) containing RNA extracted from the indicated tissues was probed with radioactively labeled txr1 and β-actin cDNA fragments.

(FIG. 3B) and (FIG. 3F) Quantitative measurement of surviving fraction. Crystal violet stained surviving cells in panels (FIG. 3B) and (FIG. 3F) were incubated with DMSO and the absorbance was measured as indicated in Experimental Procedures. The fraction of surviving cells was determined by normalizing the readouts from taxol-treated cells (lower row of panel FIG. 3B and FIG. 3F) to untreated controls (upper row in panel FIG. 3B and FIG. 3F). Results are means±SD of two independent experiments. (FIG. 3C) and (FIG. 3G) Survival curves of cells with reduced Txr1 level. Clone 18 (FIG. 3D) and M2182tTA (FIG. 3H) transfected with indicated siRNA were subjected to cell viability analysis by MTT assay. Survival rate in percentage for cells treated at indicated taxol concentration was calculated by normalizing the MTT assay readouts to the untreated control (set as 100%). Each data point represents the mean±SD from four replicates. (FIG. 3D) and (FIG. 3H) Effect of Txr1 deficiency on taxol resistance. Clone 18 (FIG. 3B) and M2182tTA cells (FIG. 3F) were transfected with siRNA (SI1 and SI2) against txr1 and with a scrambled-sequence control, and then seeded for colony formation assay in presence of the indicated concentration of taxol.

FIGS. 4A to 4E. Upregulation of Txr1 Increases Elevated Taxol Resistance in Naïve Cells. (FIG. 4A) Immunoblotting analysis. M2182tTA was infected with virus derived from pLESTTxr1HA and two permanently expressing clones R1 (FIG. 4B) and R2 (FIG. 4C) were isolated. Cell lysates of cells as indicated were subjected to immunoblotting analysis and probed with anti-Txr1 and anti-α-tubulin antibodies. (B) and (C) Effect of Txr1 overexpression on taxol resistance in naïve cells. Cells were then seeded for colony formation assay at indicated taxol concentrations in the presence or absence of 1 µg/ml Tc. (FIG. 4D) and (FIG. 4E) Quantitative measurement of surviving fraction of Clone R1 (FIG. 4D) and R2 (FIG. 4E). Crystal violet stained surviving cells in panels (B) and (C) were incubated with DMSO and the absorbance was measured as indicated in Experimental Procedures. The fraction of surviving cells was determined by normalizing the readouts from taxol-treated cells (lower row of panel FIG. 4B and FIG. 4C) to untreated controls (upper row in panel FIG. 4B and FIG. 4C).

(FIG. 5B) Northern blot analysis. 5 µg of poly(A) RNAs from indicated cells/conditions were separated and probed with radioactively labeled TSP-1 and β-actin cDNA fragments. (FIG. 5C) Luciferase assay for TSP-1 promoter activity. pTSP1.7Luc was introduced by transfection into indicated cells cultured in the presence or absence of Tc and cells were lysed for analysis 48 hr after transfection. Cell lysates were subjected to immunoblotting analysis to detect protein abundance for indicated genes (upper panel). Relative luciferase units were calculated by normalizing luciferase activity with co-transfected β-gal activity (lower panel). Results represent the mean±SD from three independent measurements. (FIG. 5D) Correlations among expression profiles of txr1 (green squares) and TSP-1 (red circles) gene expression and cellular sensitivity to taxol (blue triangles) in 13 tumor cell-lines. Data for gene expression and drug sensitivity were extracted and analyzed as described in Experimental Procedures. The Y-axis represents either expression data (for green and red curves) that have been transformed into the base 2 logarithm, or drug sensitivity (for blue curve) that was represented as the negative base 10 logarithm of G150 (−log GI50, drug concentration caused 50% of growth inhibition in molar units). The X-axis indicates each of 13 cancer cell-lines, which are 1: OVCAR4 (ovarian cancer), 2:MDA-MB-231 (breast cancer), 3: SNB-75 (renal carcinoma), 4: SF-268 (glioblastoma), 5: SK-MEL-2 (melanoma), 6: SK-OV-3 (ovarian cancer), 7:HS_578T (breast cancer), 8: ADR-RES (unknown), 9: RXF-393 (renal carcinoma), 10: U251 (glioblastoma), 11: UO-31 (renal carcinoma), 12: EKVX (non small cell lung cancer), and 13: BT-549 (breast cancer).

FIGS. 6A to 6G. TSP-1 Effects on Taxol Resistance (FIG. 6A) Dosage dependent reversal of taxol resistance in clone 18 by TSP-1. Cells treated with the indicated concentrations of TSP-1 were subjected to analysis of viability by MTT assay at various concentrations of taxol. The percentage of surviving cells was calculated by normalizing the MTT assay readouts to the untreated control, which was set as 100%. Each data point represents the mean±SD from four replicates. (FIG. 6B) TSP-1 effects on taxol sensitivity of naïve cells. Cell viability of M2182tTA cells treated with taxol or TSP-1 alone, or both concurrently (as indicated) was assessed by MTT assay. Images of wells after MTT color reaction are displayed in the left panel. Histograms represent mean±SD of four independent repeats. (FIG. 6C) The drug sensitizing effect of TSP-1 is specific to taxol. Cell viability of clone 18 cells treated with indicated drugs in the presence or absence TSP-1 was assessed by MTT assay. Histograms represent mean±SD of four independent repeat experiments. Abbreviations are: AD—250 ng/ml adriamycin, ET—1 µM etoposide, VB—10 nM vinblastine, VC—10 nM vincristine, EpoB—7.5 nM epothilone B, and TX—10 nM taxol. (FIG. 6D) TSP-1 enhancement of drug sensitivity of naïve cells is specific to taxol. Cell viability of M2182tTA cells treated with indicated drugs in the presence of absence of TSP-1 was assessed by MTT assay. Abbreviations are the same as in panel B. (FIG. 6E) TSP-1 enhances cellular sensitivity to taxol by triggering apoptotic cell death. Clone 18 cells grown on coverslips were treated with taxol or TSP-1 alone, or both as indicated. The apoptotic cells were labeled by TUNEL reagent and viewed by confocal microscopy. The bright green fluorescent nuclear spots represent TUNEL positive cells. (FIG. 6F) Immunoblotting analysis of naïve cells transfected with siRNA against TSP-1. Lysates of M2182tTA cells transfected with siRNA against TSP-1 or with a scrambled-sequence control siRNA were subjected to immunoblotting analysis and probed with anti-TSP-1 and anti-☐-tubulin antibodies. (FIG. 6G) Effect of TSP-1 deficiency on taxol resistance in naïve cells. Taxol sensitivity of M2182tTA cells transfected with siRNA against TSP-1 or a scrambled-sequence control was analyzed by colony formation assay.

FIGS. 7A to 7D. TSP-1's Signal is Mediated Through CD47 (FIG. 7A) Expression of TSP-1 receptors on cells. Clone 18 (left panels) and M2182tTA (right panels) cells were stained with anti-CD36 antibody (upper panels) and anti-CD47 (lower panels) and analyzed by flow cytometry. X-axis in histogram is the fluorescence intensity and y-axis is the frequency in percentage (maximum number is set as 100%). Cells stained with isotype control antibody were used to define the baseline and indicate as dotted lines. (FIG. 7B) Effect of 4N1K (CD47 agonist peptide) on taxol sensitivity. Clone 18 (left panels) and M2182tTA (right panel) cells treated with the indicated concentrations of TSP-1 mimetic peptides (4N1K—top panels, 4NGG-middle panels, ABT-510 lower panel) were subjected to viability analysis by MTT assay at various concentrations of taxol. The percentage of surviving cells was calculated by normalizing the MTT assay readouts to the untreated control, which was set as 100%. Each data point represents the mean±SD from four replicates. (FIG. 7C) 4N1K enhancement of drug sensitivity is specific to taxol. Cell viability of Clone 18 (left panel) and M2182tTA (right panel) cells treated with indicated drugs in the presence or absence of 4N1K was assessed by MTT assay. Abbreviations are the same as in FIG. 6, panel C. (FIG. 7D) Effect of anti-CD47 antibody and pertussis toxin on taxol cytotoxicity. Cell viability of M2182tTA (left and center panels) and clone 18 (right panel) cells treated with the indicated concentrations of taxol in the presence of 10 μg/ml of anti-CD47 antibody or control isotype IgG (left and right panels) or 0.5 μg/ml of pertussis toxin (middle panel) was assessed by MTT assay. Clone 18 cells were treated concurrently with 250 μM 4N1K.

DETAILED DESCRIPTION

Figure 2:
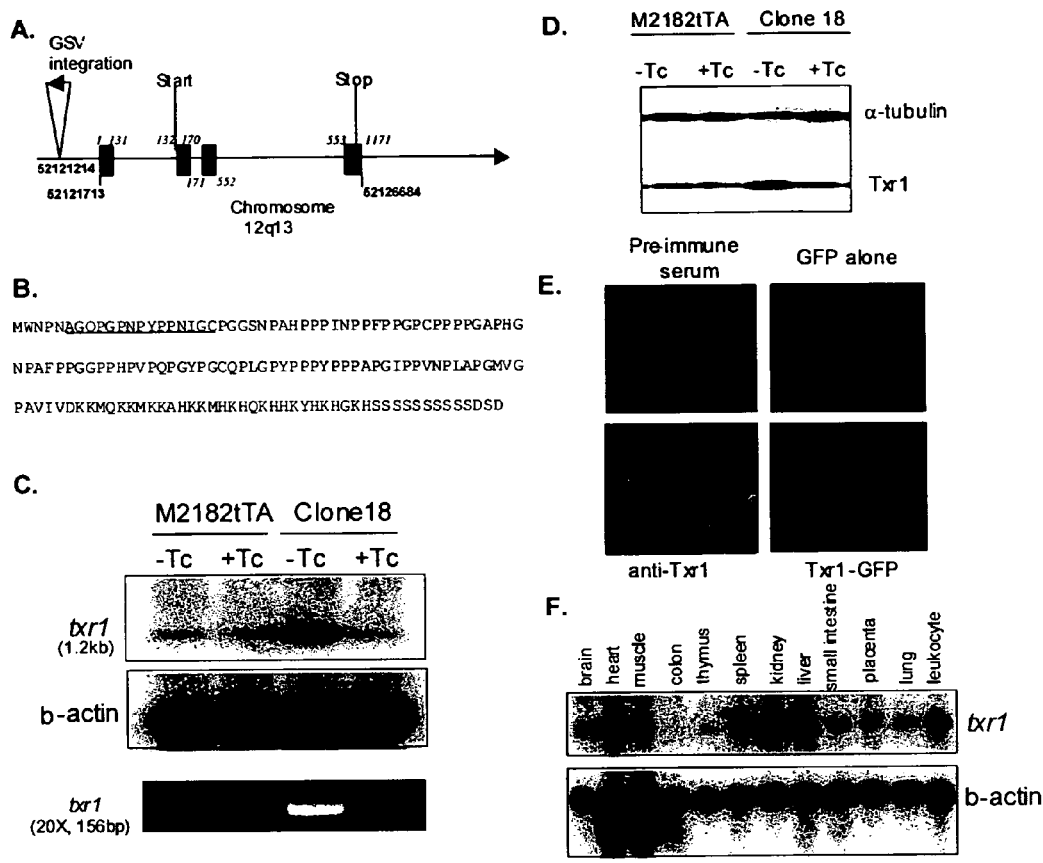
FIGS. 2A-2F. Cloning, Gene Expression, and Localization of txr1 (FIG. 2A) Schematic diagram of GSV integration site and txr1 gene structure. GSV provirus integrated (inverse triangle, arrowhead indicates the direction of transcription from the Tc-regulated promoter) at chromosome locus 12q13 (horizontal line). The genomic nucleotide coordinate for the integration site and coordinates for the start and end of txr1 transcripts are indicated below the line in bold type. Four exons of txr1 gene are shown as solid boxes and the cDNA nucleotide coordinates for the start and end of each exon are italicized. The codons initiating and terminating translation (start and stop, respectively) are indicated.

Methods and compositions for enhancing taxane sensitivity are provided. Aspects of the subject methods include administering to a subject a txr1 pathway modulatory agent in conjunction with a taxane. Also provided are txr1 polypeptides and nucleic acids encoding the same. The subject methods and compositions find use in a variety of different applications.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise: It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the invention, a more detailed review of methods according to certain embodiments is first provided, followed by a review of embodiments of utilities in which the subject methods find use and compositions that find use in embodiments of the methods.

Methods

Aspects of the invention include methods of modulating taxane resistance of a cell. By modulating is meant either enhancing or decreasing taxane resistance of a cell, where in certain embodiments the methods are methods of decreasing taxane resistance of a cell. By decreasing taxane resistance of a cell is meant that the taxane sensitivity of a cell is decreased, as measured using any convenient protocol, by 2-fold or more, such as by 5-fold or more and sometimes by 25-, 50-, 100-fold or more, as compared to a control, i.e., a cell that is not subjected to the methods of the present invention. In certain embodiments, taxane resistance of a cell is a completely reversed. In certain embodiments, the methods are methods of decreasing taxane resistance of a cell, such that the cell dies upon exposure of the cell to a taxane.

As used herein, the term "taxane" refers to compounds that have the basic taxane skeleton as a common structure feature, where the compounds have the ability to arrest cells in the G2-M phase, e.g., due to stabilization of microtubules. The basic taxane skeleton is shown below in Structural Formula (I):

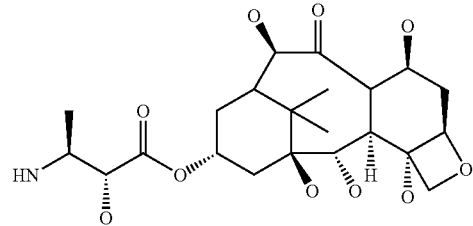

In certain embodiments, the taxane is paclitaxel. Paclitaxel is a highly derivatized diterpenoid (Wani, et al. (1971) J. Am. Chem. Soc. 93:2325-2327) which has been obtained from the harvested and dried bark of *Taxus brevifolia* (Pacific Yew) and *Taxomyces andreanae*, an endophytic fungus of the Pacific Yew (Stierle, et al. (1993) Science 60:214-216). Also included in the term "taxanes" are paclitaxel analogues, formulations, and derivatives, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel. As such, the term taxane refers to not only the common chemically available form of paclitaxel, but analogs (e.g., taxotere, as noted above) and paclitaxel conjugates (e.g., paclitaxel-PEG, paclitaxel-dextran, or paclitaxel-xylose). Also of interest are the taxanes disclosed in U.S. Pat. No. 6,800,660, the disclosure of which is herein incorporated by reference.

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Taxanes may be prepared utilizing a number of different techniques, such as those described in WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590, 267), or obtained from a variety of commercial sources, including for example, Sigma Chemical Co., St. Louis, Mo. (T7402 from *Taxus brevifolia*; or T-1912 from *Taxus yannanensis*).

Aspects of the methods include contacting a cell with an effective amount of a TXR1 pathway modulatory agent. By "TXR1 pathway modulatory agent" is meant an agent that changes or alters the activity of a pathway that includes TXR1. The amino acid sequence of human TXR1 and encoding nucleic acids thereof are provided below. The TXR1 pathway modulatory agent employed in the subject methods is one that in some way changes or alters taxane sensitivity of a cell. In other words, the agent enhances or decreases taxane sensitivity of a target cell, where modulation is determined in reference to an appropriate control.

The modulatory agent that is employed in the subject methods may be any agent that, upon contact with the cell, changes the TXR1 pathway mediated taxane sensitivity of the cell. In certain embodiments, the agent is one that enhances TXR1 pathway mediated taxane sensitivity of the cell, i.e., decreases taxane resistance of the cell.

In certain embodiments, the agent is an agent that targets TXR1. In certain embodiments, the agent may be agent that modulates, e.g., inhibits, expression of functional TXR1, i.e., is a TXR1 antagonist. Inhibition of TXR1 expression may be accomplished using any convenient means, including use of an agent that inhibits TXR1 expression, such as, but not limited to: antisense agents, RNAi agents, agents that interfere with transcription factor binding to a promoter sequence of the TXR1 gene, or inactivation of the TXR1 gene, e.g., through recombinant techniques, etc.

For example, antisense molecules can be used to down-regulate expression of TXR1 in the cell. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted repressor protein, and inhibits expression of the targeted repressor protein. Antisense molecules inhibit gene expression through various mechanisms, e.g., by reducing the amount of mRNA available for translation, through activation of RNAse H, or steric hindrance. One or a combination of antisense molecules may be administered, where a combination may include multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides—in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Oligonucleotides may be chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43-56.

In addition, the transcription level of a TXR1 can be regulated by gene silencing using RNAi agents, e.g., double-strand RNA (Sharp (1999) *Genes and Development* 13: 139-

141). RNAi, such as double-stranded RNA interference (dsRNAi) or small interfering RNA (siRNA), has been extensively documented in the nematode *C. elegans* (Fire, A., et al, Nature, 391, 806-811,1998) and routinely used to "knock down" genes in various systems. RNAi agents may be dsRNA or a transcriptional template of the interfering ribonucleic acid which can be used to produce dsRNA in a cell. In these embodiments, the transcriptional template may be a DNA that encodes the interfering ribonucleic acid. Methods and procedures associated with RNAi are also described in WO 03/010180 and WO 01/68836, all of which are incorporated herein by reference. dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety). A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma. 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

In another embodiment, the TXR1 gene is inactivated so that it no longer expresses a functional protein. By inactivated is meant that the gene, e.g., coding sequence and/or regulatory elements thereof, is genetically modified so that it no longer expresses functional a functional TXR1 protein, e.g., at least with respect to TXR1 pathway mediated taxane resistance. The alteration or mutation may take a number of different forms, e.g., through deletion of one or more nucleotide residues, through exchange of one or more nucleotide residues, and the like. One means of making such alterations in the coding sequence is by homologous recombination. Methods for generating targeted gene modifications through homologous recombination are known in the art, including those described in: U.S. Pat. Nos. 6,074,853; 5,998,209; 5,998,144; 5,948,653; 5,925,544; 5,830,698; 5,780,296; 5,776,744; 5,721,367; 5,614,396; 5,612,205; the disclosures of which are herein incorporated by reference.

Also of interest in certain embodiments are dominant negative mutants of TXR1, where expression of such mutants in the cell result in a modulation, e.g., decrease, in TXR1 pathway mediated taxane resistance of the cell. Dominant negative mutants of TXR1 are mutant proteins that exhibit dominant negative TXR1 activity. As used herein, the term "dominant-negative TXR1 activity" or "dominant negative activity" refers to the inhibition, negation, or diminution of certain particular activities of TXR1, and specifically to TXR1 mediated taxane resistance. Dominant negative mutations are readily generated for corresponding proteins. These may act by several different mechanisms, including mutations in a substrate-binding domain; mutations in a catalytic domain; mutations in a protein binding domain (e.g. multimer forming, effector, or activating protein binding domains); mutations in cellular localization domain, etc. A mutant polypeptide may interact with wild-type polypeptides (made from the other allele) and form a non-functional multimer. In certain embodiments, the mutant polypeptide will be overproduced. Point mutations are made that have such an effect. In addition, fusion of different polypeptides of various lengths to the terminus of a protein, or deletion of specific domains can yield dominant negative mutants. General strategies are available for making dominant negative mutants (see for example, Herskowitz (1987) Nature 329:219, and the references cited above). Such techniques are used to create loss of function mutations, which are useful for determining protein function. Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

In yet other embodiments, the agent is an agent that modulates, e.g., inhibits, TXR1 activity by binding to TXR1. For example, small molecules that bind to the TXR1 and inhibit its taxane sensitivity modulatory activity are of interest. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below.

In yet other embodiments, the TXR1 binding agent may be an antibody agent, e.g. a neutralizing antibody agent. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. Antibodies that bind specifically to the TXR1 target are referred to as anti-TXR1 target antibodies. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be polyclonal antibodies, although monoclonal antibodies are employed in certain embodiments because they may be reproduced by cell culture or recombinantly, and can be modified to reduce their antigenicity.

Polyclonal antibodies can be raised by a standard protocol by injecting a production animal with an antigenic composition, formulated as described above. See, e.g., Harlow and Lane, Antibodies: A Laboratory Manual, Cold Spring Harbor Laboratory, 1988. In one such technique, a TXR1 antigen comprising an antigenic portion of the TXR1 target polypeptide is initially injected into any of a wide variety of mammals (e.g., mice, rats, rabbits, sheep or goats). When utilizing an entire protein, or a larger section of the protein, antibodies may be raised by immunizing the production animal with the protein and a suitable adjuvant (e.g., Fruend's, Fruend's complete, oil-in-water emulsions, etc.) When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. The peptide-conjugate is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. The immortal cell line utilized is preferably selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

In certain embodiments, the immortal fusion partners utilized are derived from a line that does not secrete immunoglobulin. The resulting fused cells, or hybridomas, are cultured under conditions that allow for the survival of fused, but not unfused, cells and the resulting colonies screened for the production of the desired monoclonal antibodies. Colonies producing such antibodies are cloned, expanded, and grown so as to produce large quantities of antibody, see Kohler and Milstein, 1975 Nature 256:495 (the disclosures of which are hereby incorporated by reference).

Large-quantities of monoclonal antibodies from the secreting hybridomas may then be produced by injecting the clones into the peritoneal cavity of mice and harvesting the ascites fluid therefrom. The mice, preferably primed with pristane, or some other tumor-promoter, and immunosuppressed chemically or by irradiation, may be any of various suitable strains known to those in the art. The ascites fluid is harvested from the mice and the monoclonal antibody purified therefrom, for example, by CM Sepharose column or other chromatographic means. Alternatively, the hybridomas may be cultured in vitro or as suspension cultures. Batch, continuous culture, or other suitable culture processes may be utilized. Monoclonal antibodies are then recovered from the culture medium or supernatant.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell.). When antibody gene synthesis is induced in the transfected host, the heavy and light chain proteins self-assemble to produce active antibodies that can be detected by screening with the antigen or immunogen.

In certain embodiments, recombinant antibodies are produced in a recombinant protein production system which correctly glycosylates and processes the immunoglobulin chains, such as insect or mammalian cells. An advantage to using insect cells, which utilize recombinant baculoviruses for the production of antibodies, is that the baculovirus system allows production of mutant antibodies much more rapidly than stably transfected mammalian cell lines. In addition, insect cells have been shown to correctly process and glycosylate eukaryotic proteins, which prokaryotic cells do not. Finally, the baculovirus expression of foreign protein has been shown to constitute as much as 50-75% of the total cellular protein late in viral infection, making this system an excellent means of producing milligram quantities of the recombinant antibodies.

Antibodies with a reduced propensity to induce a violent or detrimental immune response in humans (such as anaphylactic shock), and which also exhibit a reduced propensity for priming an immune response which would prevent repeated dosage with the antibody therapeutic or imaging agent are preferred for use in the invention. Thus, humanized, chimeric, or xenogenic human antibodies, which produce less of an immune response when administered to humans, are preferred for use in the present invention.

Chimeric antibodies may be made by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference). Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

Alternatively, polyclonal or monoclonal antibodies may be produced from animals that have been genetically altered to produce human immunoglobulins. Techniques for generating such animals, and deriving antibodies therefrom, are described in U.S. Pat. Nos. 6,162,963 and 6,150,584, incorporated fully herein by reference.

Alternatively, single chain antibodies (Fv, as described below) can be produced from phage libraries containing human variable regions. See U.S. Pat. No. 6,174,708. In addition to entire immunoglobulins (or their recombinant counterparts), immunoglobulin fragments comprising the epitope binding site (e.g., Fab', $F(ab')_2$, or other fragments) are useful as antibody moieties in the present invention. Such antibody fragments may be generated from whole immunoglobulins by ficin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., polyglycine or another sequence which does not form an alpha helix or beta sheet motif).

Fv fragments are heterodimers of the variable heavy chain domain ($V_H$) and the variable light chain domain ($V_L$). The heterodimers of heavy and light chain domains that occur in whole IgG, for example, are connected by a disulfide bond. Recombinant Fvs in which $V_H$ and $V_L$ are connected by a peptide linker are typically stable, see, for example, Huston et al., Proc. Natl. Acad, Sci. USA 85:5879-5883 (1988) and Bird et al., Science 242:423-426 (1988), both fully incorporated herein, by reference.

In addition, derivatized immunoglobulins with added chemical linkers, detectable moieties, such as fluorescent dyes, enzymes, substrates, chemiluminescent moieties and the like, or specific binding moieties, such as streptavidin, avidin, or biotin, and the like may be utilized in the methods and compositions of the present invention. For convenience, the term "antibody" or "antibody moiety" will be used throughout to generally refer to molecules which specifically bind to an epitope of the TXR1 protein targets, although the term will encompass all immunoglobulins, derivatives, fragments, recombinant or engineered immunoglobulins, and modified immunoglobulins, as described above.

Candidate-antibodies can be tested for activity by any suitable standard means. As a first screen, the antibodies may be tested for binding against the immunogen, or protein. As a second screen, candidates may be tested for binding to an appropriate cell line. For these screens, the candidate antibody may be labeled for detection. After selective binding to the protein target is established, the candidate antibody agent may be tested for appropriate activity (i.e., the ability to increase taxane sensitivity to cells) in an in vitro or in vivo model.

In yet other embodiments, the TXR1 pathway modulatory agent is an agent that modulates another member of the target TXR1 pathway, e.g., a member of the pathway upstream or downstream from TXR1. The modulatory agent may directly target this non-TXR1 member of the pathway, or indirectly target this member of pathway, such that activity of the non-TXR1 member is modulated.

For example, in certain embodiments, the TXR1 pathway modulatory agent is an agent that modulates TSP-1. TSP-1 is an extracelluar matrix (ECM) bound adhesive glycoprotein secreted from a wide variety of epithelial and mesenchymal cells (de Fraipont, F., Nicholson, A. C., Feige, J. J., and Van Meir, E. G. (2001). Thrombospondins and tumor angiogenesis. Trends Mol Med 7, 401-407). The protein and encoding nucleic acid sequence for human TSP-1 have been deposited with Genbank and assigned accession no. NM_003246, by which they are readily obtained.

In these embodiments, the TSP-1 genes, gene fragments, or the encoded protein or protein fragments, e.g., peptides, are useful to modulate, e.g., enhance, TSP-1 activity in the cell. Inhibition or upregulation of expression is achieved in a number of ways. Coding sequences may be introduced to increase expression levels. Binding antagonists, for example, a peptide that mimics TSP-1 binding and retains TSP-1 activity, at least with respect to increasing taxane sensitivity, may be used. Protocols analogous to those described above with respect to TXR1 may be employed.

Introduction of an expression vector encoding a polypeptide can be used to express the encoded product in cells lacking the sequence, or to over-express the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an anti-sense oligonucleotide; encode a dominant negative mutation, or dominant or constitutively active mutations of native sequences; altered regulatory sequences, etc.

A variety of methods can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

A variety of host-expression vector systems may be utilized to express a genetic coding sequence. Expression constructs may contain promoters derived from the genome of mammalian cells, e.g., metallothionein promoter, elongation factor promoter, actin promoter, etc., from mammalian viruses, e.g., the adenovirus late promoter; the vaccinia virus 7.5K promoter, SV40 late promoter, cytomegalovirus, etc.

In mammalian host cells, a number of viral-based expression systems may be utilized, e.g. retrovirus, lentivirus, adenovirus, herpesvirus, and the like. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the gene product in infected hosts (see Logan & Shenk, 1984, Proc. Natl. Acad. Sci. USA 81:3655-3659). Specific initiation signals may also be required for efficient translation of inserted gene product coding sequences. These signals include the ATG initiation codon and adjacent sequences. Standard systems for generating adenoviral vectors for expression on inserted sequences are available from commercial sources, for example the Adeno-X™ expression system from Clontech (Clontechniques (January 2000) p. 10-12).

In cases where an entire gene, including its own initiation codon and adjacent sequences, is inserted into the appropriate expression vector, no additional translational control signals may be needed. However, in cases where only a portion of the gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516-544).

In representative embodiments, methods are used that achieve a high efficiency of transfection, and therefore circumvent the need for using selectable markers. These may include adenovirus infection (see, for example Wrighton, 1996, J. Exp. Med. 183: 1013; Soares, J. Immunol., 1998, 161: 4572; Spiecker, 2000, J. Immunol 164: 3316; and Weber, 1999, Blood 93: 3685); and lentivirus infection (for example, International Patent Application WO000600; or WO9851810). Adenovirus-mediated gene transduction of endothelial cells has been reported with 100% efficiency. Retroviral vectors also can have a high efficiency of infection with endothelial cells, with reported infection efficiencies of 40-77%. Other vectors of interest include lentiviral vectors, for examples, see Barry et al. (2000) Hum Gene Ther 11 (2):323-32; and Wang et al. (2000) Gene Ther 7(3):196-200.

Viral vectors include retroviral vectors (e.g. derived from MoMLV, MSCV, SFFV, MPSV, SNV etc), lentiviral vectors (e.g. derived from HIV-1, HIV-2, SIV, BIV, FIV etc.), adeno-associated virus (AAV) vectors, adenoviral vectors (e.g. derived from Ad5 virus), SV40-based vectors, Herpes Simplex Virus (HSV)-based vectors etc. A vector construct may include drug resistance genes (neo, dhfr, hprt, gpt, bleo, puro etc) enzymes (β-galactosidase, alkaline phosphatase etc) fluorescent genes (e.g. GFP, RFP, BFP, YFP) or surface markers (e.g. CD24, NGFr, Lyt-2 etc).

The gene or protein may be introduced into tissues or host cells by any number of routes, including viral infection, microinjection, or fusion of vesicles. Jet injection may also be used for intra-muscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells.

Once the gene corresponding to a selected polynucleotide is identified, its expression can be regulated in the cell to which the gene is native. For example, an endogenous gene of a cell can be regulated by an exogenous regulatory sequence as disclosed in U.S. Pat. No. 5,641,670; the disclosure of which is herein incorporated by reference.

Also of interest in these embodiments is the administration of TSP-1 itself or active fragments, as well as mimetics, thereof. Biologically active fragments, mutants, or analogues of TSP-1 are tested for the ability to enhance taxane sensitivity. Fragments are recombinantly produced or generated by enzymatic digestion. Fragments and analogues of human thrombospondin are known in the art (e.g., as described in U.S. Pat. No. 5,192,744 or U.S. Pat. No. 5,840,692; the disclosure of which are herein incorporated by reference). Additional representative peptides having TSP-1 activity are disclosed in: published United States patent applications 20040143113, 20040110131, 20040053392, 20030171298, 20030114529, 10 20020099027, 20020022592; the disclosures of which applications are herein incorporated by reference. Enhancement of taxane sensitivity is measured using methods, e.g., the methods reported below.

In certain of these embodiments, the amount of TSP-1 or peptide fragment thereof that is administered to the host is less than that which is administered in certain prior art methods where TSP-1 is administered as the sole active agent, and not as an agent to enhance sensitivity to a taxane. The amount that is administered in these embodiments may be 2 fold less, 5 fold less, 10 fold less, 20 fold less, 25 fold less or 50 fold less, etc. Furthermore, in certain embodiments synergistic results are observed, in which the observed results are significantly better that the expected results of administering TSP-1 (or a fragment thereof and taxane together.

Also of interest are small molecule mimetics of the above-described proteins or active fragments thereof, such as those described above in connection with TXR1.

In yet other embodiments, the TXR1 pathway modulatory agent is an agent that modulates, e.g., enhances, functional CD47. The human CD47 amino acid sequence and encoding nucleic acid therefore have been deposited with GENBANK and given an accession no. of NM_001025079. In these embodiments, approaches analogous to those described above for modulating TXR1 may be employed.

As demonstrated above, a variety of different types of TXR1 pathway modulatory agents may be employed in the subject methods, where certain types of agents are reviewed above. As demonstrated above, the agents employed may target TXR1 directly, or another member of the TXR1 pathway, e.g., TSP-1, CD47, etc. In certain embodiments, the agent administered is not TSP-1 or a direct modulatory agent thereof, e.g., nucleic acid encoding the same.

As reviewed above, aspects of the subject methods include contacting a cell with a taxane in conjunction with a TXR1 pathway modulatory agent. By "in conjunction with" is meant that the TXR1 pathway modulatory agent is administered anywhere from simultaneously to up to 5 hours or more, e.g., 10 hours, 15 hours, 20 hours or more, prior to or after the taxane agent. Thus, the TXR1 pathway modulatory agent and the taxane agent may be administered either: (a) sequentially, with the TXR1 pathway modulatory agent being administered prior to or after the taxane agent or (b) simultaneously, with the TXR1 pathway modulatory agent being administered to the subject at the same time as the taxane agent. Where the TXR1 pathway modulatory agent is administered simultaneously with the taxane agent, the two components may be administered as either a single, combined composition or as two distinct compositions that are simultaneously contacted with the cell, e.g., that are simultaneously administered to the subject.

Contact of the cell with the TXR1 modulatory agent may occur using any convenient protocol. The protocol may provide for in vitro or in vivo contact of the modulatory agent with the target cell, depending on the location of the target cell. Contact may or may not include entry of the agent into the cell. For example, where the target cell is an isolated cell and the modulatory agent is an agent that modulates expression of TXR1, the modulatory agent may be introduced directly into the cell under cell culture conditions permissive of viability of the target cell. Such techniques include, but are not necessarily limited to: viral infection, transfection, conjugation, protoplast fusion, electroporation, particle gun technology, calcium phosphate precipitation, direct microinjection, viral vector delivery, and the like. The choice of method is generally dependent on the type of cell being contacted and the nature of the modulatory agent, and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

Alternatively, where the target cell or cells are part of a multicellular organism, the modulatory agent may be administered to the organism or subject in a manner such that the agent is able to contact the target cell(s), e.g., via an in vivo or ex vivo protocol. By "in vivo," it is meant in the target construct is administered to a living body of an animal. By "ex vivo" it is meant that cells or organs are modified outside of the body. Such cells or organs are typically returned to a living body.

In the subject methods, the active agent(s) may be administered to the targeted cells using any convenient means capable of resulting in the desired activity. Thus, the agent can be incorporated into a variety of formulations, e.g., pharmaceutically acceptable vehicles, for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, it may be introduced into tissues or host cells by any number of routes, including viral infection, microinjection, or fusion of vesicles. Jet injection may also be used for intramuscular administration, as described by Furth et al (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells. For nucleic acid therapeutic agents, a number of different delivery vehicles find use, including viral and non-viral vector systems, as are known in the art.

Liposomes may be used for gene or protein delivery in vivo and in vitro. The liposomes employed in the present invention can be prepared using any one of a variety of conventional liposome preparatory techniques. As will be readily apparent to those skilled in the art, such conventional techniques include sonication, chelate dialysis, homogenization, solvent infusion coupled with extrusion, freeze-thaw extrusion, microemulsification, as well as others. These techniques, as well as others, are discussed, for example, in U.S. Pat. No. 4,728,578, U.K. Patent Application G.B. 2193095 A, U.S. Pat. No. 4,728,575, U.S. Pat. No. 4,737,323, International Application PCT/US85/01161, Mayer et al., Biochimica et Biophysica Acta, Vol. 858, pp. 161-168 (1986), Hope et al., Biochimica et Biophysica Acta, Vol. 812, pp. 55-65 (1985), U.S. Pat. No. 4,533,254, Mahew et al., Methods In Enzymology, Vol. 149, pp. 64-77 (1987), Mahew et al., Biochimica et Biophysica Acta, Vol. 75, pp. 169-174 (1984), and Cheng et al., Investigative Radiology, Vol. 22, pp. 47-55 (1987). A solvent free system similar to that described in International Application PCT/US85/01161 may be employed in preparing the liposome constructions.

The materials that are utilized in preparing the liposomes include any of the materials or combinations thereof known to those skilled in the art as suitable in liposome construction.

The lipids used may be of either natural or synthetic origin. Such materials include, but are not limited to, lipids such as cholesterol, phosphatidylcholine, phosphatidylethanolamine, phosphatidylserine, phosphatidylglycerol, phosphatidic acid, phosphatidylinositol, lysolipids, fatty acids, sphingomyelin, glycosphingolipids, glucolipids, glycolipids, sulphatides, lipids with amide, ether, and ester-linked fatty acids, polymerizable lipids, and combinations thereof. As one skilled in the art will recognize, the liposomes may be synthesized in the absence or presence of incorporated glycolipid, complex carbohydrate, protein or synthetic polymer, using conventional procedures. The surface of a liposome may also be modified with a polymer, such as, for example, with polyethylene glycol (PEG), using procedures readily apparent to those skilled in the art. Any species of lipid may be used, with the sole proviso that the lipid or combination of lipids and associated materials incorporated within the lipid matrix should form a bilayer phase under physiologically relevant conditions. As one skilled in the art will recognize, the composition of the liposomes may be altered to modulate the biodistribution and clearance properties of the resulting liposomes.

The membrane bilayers in these structures typically encapsulate an aqueous volume, and form a permeability barrier between the encapsulated volume and the exterior solution. Lipids dispersed in aqueous solution spontaneously form bilayers with the hydrocarbon tails directed inward and the polar headgroups outward to interact with water. Simple agitation of the mixture usually produces multilamellar vesicles (MLVs), structures with many bilayers in an onion-like form having diameters of 1-10 .mu.m (1000-10,000 nm). Sonication of these structures, or other methods known in the art, leads to formation of unilamellar vesicles (UVs) having an average diameter of about 30-300 nm. However, the range of 50 to 200 nm is considered to be optimal from the standpoint of, e.g., maximal circulation time in vivo. The actual equilibrium diameter is largely determined by the nature of the phospholipid used and the extent of incorporation of other lipids such as cholesterol. Standard methods for the formation of liposomes are known in the art, for example, methods for the commercial production of liposomes are described in U.S. Pat. No. 4,753,788, and U.S. Pat. No. 4,935,171.

Polymerized liposomes are self-assembled aggregates of lipid molecules, and are described in U.S. Pat. Nos. 5,512,294, 6,132,764, and U.S. Pat. Application 20020071843. The hydrophobic tail groups of polymerizable lipids are derivatized with polymerizable groups, such as diacetylene groups, which irreversibly cross-link, or polymerize, when exposed to ultraviolet light or other radical, anionic or cationic, initiating species, while maintaining the distribution of functional groups at the surface of the liposome. The resulting polymerized liposome particle is stabilized against fusion with cell membranes or other liposomes and stabilized towards enzymatic degradation. The size of the polymerized liposomes can be controlled by extrusion or other methods known to those skilled in the art. Polymerized liposomes may be comprised of polymerizable lipids, but may also comprise saturated and non-alkyne, unsaturated lipids. The polymerized liposomes can be a mixture of lipids, which provide different functional groups on the hydrophilic exposed surface. For example, some hydrophilic head groups can have functional surface groups, for example, biotin, amines, cyano, carboxylic acids, isothiocyanates, thiols, disulfides, $\alpha$-halocarbonyl compounds, $\alpha,\beta$-unsaturated carbonyl compounds and alkyl hydrazines. These groups can be used for attachment of nucleic acid sequences.

Molecules such as peptides, DNA or RNA may be attached to the outside of the liposome for gene therapy applications. The liposome structure can be readily injected and form the basis for both sustained release and drug delivery to specific cell types, or parts of the body.

For use in the above described formulations, the agents or derivatives therefrom may be synthesized and stored as a solid lyophilized powder which is reconstituted into a pharmaceutically acceptable liquid immediately prior to use. Such formulations are usually preferred because it is recognized by those skilled in the art that lyophilized preparations generally maintain pharmaceutical activity better over time than their liquid counterparts.

Where the active agent is a peptide, the peptides may be formulated as a liquid, e.g. comprising a buffer at a concentration of from about 1 mM to about 50 mM that functions to maintain the pH, wherein the anion of said buffer may be selected from the group consisting of acetate, phosphate, carbonate, succinate, citrate, borate, tartrate, fumarate and lactate; and an alcohol which may be selected from the group consisting of mannitol, sorbitol, ribotol, arabitol, xylitol, inositol, galactitol, methanol, ethanol and glycerol. Other additives may include amino acids such as methionine, arginine, lysine, glutamic acid, cysteine, glutathione, and the like, where amino acids are generally present in concentrations ranging from about 1 mM to about 100 mM. Various sugars are optionally included in the formulations, including, for example, glucose, sucrose, lactose, fructose, trehalose, mannose, and the like. Additive sugars are generally present in concentrations ranging from about 1% to about 10%.

The dose levels can vary as a function of the specific compound, the nature of the delivery vehicle, and the like. Dosages for a given compound are readily determinable by those of skill in the art by a variety of means.

As reviewed above, the subject methods result in modulation of taxane sensitivity of a target cell or cells, where the target cell(s) may be in vitro or in vivo. In certain embodiments, the subject methods result in an increase of taxane sensitivity of a target cell(s). In certain embodiments, the methods result in a decrease in taxane resistance of cell, e.g., as measured using the assay protocols described in the experimental section below.

The above methods find use in a variety of different applications. Applications according to certain embodiments are now reviewed in the followin Utility section.

Utility

Embodiments of the methods find use in therapeutic applications in which taxane administration is indicated. One therapeutic application of the invention is the treatment of cellular proliferative disease conditions, e.g., cancers and related conditions characterized by abnormal cellular proliferation concomitant. Such disease conditions include cancer/neoplastic diseases and other diseases characterized by the presence of unwanted cellular proliferation, e.g., hyperplasias, and the like.

By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

The subject methods find use in, among other applications, the treatment of cellular proliferative disease conditions, including neoplastic disease conditions, i.e., cancers. In such applications, an effective amount of an active agent is administered to the subject in need thereof. Treatment is used broadly as defined above, e.g., to include at least an amelioration in one or more of the symptoms of the disease, as well as a complete cessation thereof, as well as a reversal and/or complete removal of the disease condition, e.g., cure.

There are many disorders associated with a dysregulation of cellular proliferation, i.e., cellular hyperproliferative disorders. The conditions of interest include, but are not limited to, the following conditions.

The subject methods may be employed in the treatment of a variety of conditions where there is proliferation and/or migration of smooth muscle cells, and/or inflammatory cells into the intimal layer of a vessel, resulting in restricted blood flow through that vessel, i.e., neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Diseases where there is hyperproliferation and tissue remodelling or repair of reproductive tissue, e.g., uterine, testicular and ovarian carcinomas, endometriosis, squamous and glandular epithelial carcinomas of the cervix, etc. are reduced in cell number by administration of the subject compounds Tumors of interest for treatment include carcinomas, e.g. colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies, e.g. neuroblastoma, gliomas, etc.; hematological malignancies, e.g. childhood acute leukaemia, acute myelogenous leukemias, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Some cancers of particular interest include breast cancers, which are primarily adenocarcinoma subtypes. Ductal carcinoma in situ is the most common type of noninvasive breast cancer. In DCIS, the malignant cells have not metastasized through the walls of the ducts into the fatty tissue of the breast. Infiltrating (or invasive) ductal carcinoma (IDC) has metastasized through the wall of the duct and invaded the fatty tissue of the breast. Infiltrating (or invasive) lobular carcinoma (ILC) is similar to IDC, in that it has the potential metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematogenous routes to distant sites. Any organ may be involved by metastases, but lungs and liver are common sites.

Other hyperproliferative diseases of interest relate to epidermal hyperproliferation, tissue remodelling and repair. For example, the chronic skin inflammation of psoriasis is associated with hyperplastic epidermal keratinocytes as well as infiltrating mononuclear cells, including CD4+ memory T cells, neutrophils and macrophages.

The methods of the present invention can provide a highly general method of treating many-if not most-malignancies, including tumors derived from cells selected from skin, connective tissue, adipose, breast, lung, stomach, pancreas, ovary, cervix, uterus, kidney, bladder, colon, prostate, central nervous system (CNS), retina and blood, and the like. Representative cancers of interest include, but are not limited to: Head/Neck and Lung tissue (e.g., Head and neck squamous cell carcinoma, Non-small cell lung carcinoma, Small cell lung carcinoma) Gastrointestinal tract and pancreas (e.g., Gastric carcinoma, Colorectal adenoma, Colorectal carcinoma, Pancreatic carcinoma); Hepatic tissue (e.g., Hepatocellular carcinoma), Kidney/urinary tract (e.g., Dysplastic urothelium, Bladder carcinoma, Renal carcinoma, Wilms tumor) Breast (e.g., Breast carcinoma); Neural tissue (e.g., Retinoblastoma, Oligodendroglioma, Neuroblastoma, Meningioma malignant; Skin (e.g., Normal epidermis, Squamous cell carcinoma, Basal cell carcinoma, Melanoma, etc.); Hematological tissues (e.g., Lymphoma, CML chronic myeloid leukemia, APL acute promyelocytic leukemia, ALL acute lymphoblastic leukemia, acute myeloid leukemia, etc.); and the like.

The conditions of non-clinical in vitro use are readily determined by one of ordinary skill in the art. Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment. For clinical in vivo use, the cytotoxic agent of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 100 ml of normal saline to which 5 to 10 ml of human serum albumin can be added. Dosages will be 10 μg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Applications in which the methods and compositions of embodiments of the invention find use also include, but are not limited to: those described in published United States Patent Application Nos. 20050026996; 20050020635; 20040186305; 20040157786; 20040152673; 20040152644; 20040152643; 20040152642; 20040138267; 20040127551; 20040122081; 20040122055; 20040097579; 20040087547; 20040013660; 20030220391; 20030203961; 20030203960; 20030181473; 20030175913; 20030153539; 20030125374; 20030105156; 20030097024; 20030069415; 20030050485; 20030035830; 20030013889; 20020197245; 20020182204; 20020137955; 20020052518; 20020052403; 20020031505; 20020016356; 20020013484; 20020012976; 20020002292; 20010053857; 20010041706; 20010041194; and 20010023255; the disclosures of which are herein incorporated by reference.

The methods may be used in conjunction with other treatment modalities. Embodiments of the invention may be used in conjunction with any current or future therapy. Specific additional therapies of interest including surgery, radiation, hormonal therapy, chemotherapy, immunotherapy, cryotherapy, etc.

Screening Assays

The availability of purified TXR1, as described below, and other components in the TXR1 pathway, e.g., TSP-1 etc., allows in vitro reconstruction of the pathway. Two or more of the components may be combined in vitro, and the behavior assessed in terms of activation of transcription of specific target sequences; modification of protein components, e.g. proteolytic processing, phosphorylation, methylation, etc.; ability of different protein components to bind to each other, etc. The components may be modified by sequence deletion, substitution, etc. to determine the functional role of specific residues.

Drug screening may be performed using an in vitro model, a genetically altered cell or animal, or purified TXR1 protein. One can identify ligands or substrates that compete with, modulate or mimic the action of TXR1. Areas of investigation include the development of treatments as a cardioprotective agent; for treatment of hypertension; for activity relating to the release of prolactin, regulation of growth hormone release; etc.

Drug screening identifies agents that mimic TXR1 activity, either as an antagonist or as an agonist. A wide variety of assays may be used for this purpose, including labeled in vitro protein-protein binding assays, electrophoretic mobility shift assays, immunoassays for protein binding, and the like. Knowledge of the 3-dimensional structure of TXR1, derived from crystallization of purified synthetic TXR1 protein, leads to the rational design of small drugs that specifically inhibit TXR1 activity.

The term "agent" as used herein describes any molecule, e.g. protein or pharmaceutical, with the capability of altering or mimicking the physiological function of TXR1. Generally, a plurality of assay mixtures are run in parallel with different agent concentrations to obtain a differential response to the various concentrations. Typically one of these concentrations serves as a negative control, i.e., at zero concentration or below the level of detection.

Candidate agents encompass numerous chemical classes, such as organic molecules, e.g., small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and anti-digoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment of hypertension, etc. The compounds may also be used to enhance TXR1 function as a cardioprotective agent; for treatment of hypertension; for appetite suppression, for activity relating to the release of prolactin, regulation of growth hormone release; etc. The agents may be administered in a variety of ways, orally, topically, parenterally e.g. subcutaneously, intraperitoneally, by viral infection, intravascularly, etc. Depending upon the manner of introduction, the compounds may be formulated in a variety of ways. The concentration of therapeutically active compound in the formulation may vary from about 0.1-10 wt %.

As such, also provided by the subject invention are screening assays designed to find TXR1 pathway modulatory agents of the invention, where such agents may find use in a variety of applications, including as therapeutic agents, as described above. The screening methods may be assays which provide for qualitative/quantitative measurements of TXR1 pathway mediated taxane resistance in the presence of a particular candidate therapeutic agent. The screening method may be an in vitro or in vivo format, where both formats are readily developed by those of skill in the art.

Pharmaceutical Preparations

Also provided are pharmaceutical preparations of the subject compounds. The subject compounds can be incorporated into a variety of formulations for administration to a subject. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. The formulations may be designed for administration via a number of different routes, including oral, buccal, rectal, parenteral, intraperitoneal, intradermal, transdermal, intracheal, etc., administration.

In pharmaceutical dosage forms, the compounds may be administered in the form-f their pharmaceutically acceptable salts, or they may also be used alone or in appropriate association, as well as in combination, with other pharmaceutically active compounds. The following methods and excipients are merely exemplary and are in no way limiting.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain-aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Optionally, the pharmaceutical composition may contain other pharmaceutically acceptable components, such a buffers, surfactants, antioxidants, viscosity modifying agents, preservatives and the like. Each of these components is well-known in the art. See, for example, U.S. Pat. No. 5,985,310, the disclosure of which is herein incorporated by reference.

Other components suitable for use in the formulations of the present invention can be found in Remington's Pharmaceutical Sciences, Mace Publishing Company, Philadelphia, Pa., 17th ed. (1985). In an embodiment, the aqueous cyclodextrin solution further comprise dextrose, e.g., about 5% dextrose.

Dosage levels of the order of from about 0.01 mg to about 140 mg/kg of body weight per day are useful in representative embodiments, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day. Those of skill will readily appreciate that dose levels can vary as a function of the specific compound, the severity of the symptoms and the susceptibility of the subject to side effects. Preferred dosages for a given compound are readily determinable by those of skill in the art by a variety of means.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

As such, unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular peptidomimetic compound employed and the effect to be achieved, and the pharmacodynamics associated with each compound in the host.

Kits & Systems

Also provided are kits and systems that find use in practicing the subject methods, as described above. For example, kits and systems for practicing the subject methods may include one or more pharmaceutical formulations. As such, in certain embodiments the kits may include a single pharmaceutical composition, present as one or more unit dosages, where the composition may include one or more expression/activity inhibitor compounds. In yet other embodiments, the kits may include two or more separate pharmaceutical compositions, each containing a different active compound.

In addition to the above comments, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The term "system" as employed herein refers to a collection of two or more different active agents, present in a single or disparate composition, that are brought together for the purpose of practicing the subject methods.

TXR1 Polypeptides

The amino acid sequence of human TXR1 is provided in FIG. 2B (SEQ ID NO:16). Nucleic acids encoding all or significant portions of TXR1 polypeptides include those deposited and assigned accession nos. NM_001005355; NM_018457; NP_001005355; NM_001005354 and NP_001005354, as reviewed in greater detail below in the Experimental Section.

For use in the subject methods, native TXR1 or modifications thereof may be used. Peptides of interest as immunogens and for screening methods, e.g. competitive receptor binding, include fragments of at least about 12 contiguous amino acids, more usually at least about 20 contiguous amino acids, and may comprise 30 or more amino acids, up to the provided peptide, and may extend further to comprise other sequences present in the precursor protein. Peptides of interest for therapeutic purposes may include all or substantially all of the provided peptide, or may comprise fragments thereof that retain the biological activity of TXR1. Such peptides may be amidated, and may comprise substantially all of the mature peptide sequence, i.e. At least about 20 contiguous amino acid resides, at least about 30 contiguous amino acid resides, and may comprise 45 contiguous amino acids residues, or more. Deletions may extend from residue 1 through 10 of the peptide, and may further delete additionally amino acids at residues 10-15 or more. Smaller deletions, of from 1 to 5 amino acids, may be deleted in the N-terminus.

The sequence of the TXR1 polypeptide may be altered in various ways known in the art to generate targeted changes in sequence. The polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threnodies); (lysine, arginine); or (phenylalanine, tyrosine).

Modifications of interest that do not alter primary sequence include chemical dramatization of polypeptides, e.g., acetylation, or carboxylate. Also included are modifications of glycosylation, e.g. Those made by modifying the glycosylation patterns of a polypeptide during its synthesis and processing or in further processing steps; e.g. By exposing the polypeptide to enzymes which affect glycosylation, such as mammalian glycosylation or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) J. Biol. Chem. 275:23783-23789). Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

TXR1 Nucleic Acids

The invention includes nucleic acids having a sequence that encodes TXR1; nucleic acids that hybridize under stringent conditions, particularly conditions of high stringency, to such a sequence; genes-corresponding to the provided nucleic acids; sequences encoding TXR1 polypeptides; and fragments and derivatives thereof. Other nucleic acid compositions contemplated by and within the scope of the present invention will be readily apparent to one of ordinary skill in the art when provided with the disclosure here.

The nucleic acids of the invention include nucleic acids having sequence similarity or sequence identity to specific sequences deposited and assigned accession nos. NM_001005355; NM_018457; NP_001005355; NM_001005354 and NP_001005354. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under stringent conditions, for example, at 50° C. or higher and 0.1×SSC (9 mM saline/0.9 mM sodium citrate). Hybridization methods and conditions are well known in the art, see, e.g., U.S. Pat. No. 5,707,829. Nucleic acids that are substantially identical to the provided nucleic acid sequence, e.g. allelic variants, genetically altered versions of the gene, etc., bind to the deposited sequences under stringent hybridization conditions. By using probes, particularly labeled probes of DNA sequences, one can isolate homologous or related genes. The source of homologous genes can be any species, e.g. primate species, particularly human; rodents, such as rats and mice; canines, felines, bovines, ovines, equines, fish, yeast, nematodes, etc.

In one embodiment, hybridization is performed using at least 18 contiguous nucleotides (nt) of a known deposited sequence, or a DNA encoding the TXR1 polypeptide. Such a probe will preferentially hybridize with a nucleic acid comprising the complementary sequence, allowing the identification and retrieval of the nucleic acids that uniquely hybridize to the selected probe. Probes of more than 18 nt can be used, e.g., probes of from about 18 nt to about 25, 50, 100, 250, or 500 nt, but 18 nt usually represents sufficient sequence for unique identification.

Nucleic acids of the invention also include naturally occurring variants of the nucleotide sequences (e.g., degenerate variants, allelic variants, etc.). Variants of the nucleic acids of the invention are identified by hybridization of putative variants with nucleotide sequences disclosed herein, preferably by hybridization under stringent conditions. For example, by using appropriate wash conditions, variants of the nucleic acids of the invention can be identified where the allelic variant exhibits at most about 25-30% base pair (bp) mismatches relative to the selected nucleic acid probe. In general, allelic variants contain 15-25% bp mismatches, and can contain as little as even 5-15%, or 2-5%, or 1-2% bp mismatches, as well as a single bp mismatch.

The invention also encompasses homologs corresponding to the nucleic acids, where the source of homologous genes can be any mammalian species, e.g., primate species, particularly human; rodents, such as rats; canines, felines, bovines, ovines, equines, fish, yeast, nematodes, etc. Between mammalian species, e.g., human and mouse, homologs generally have substantial sequence similarity, e.g., at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 contiguous nt long, more usually at least about 30 nt long, and may extend to the complete sequence that is being compared. Algorithms for sequence analysis are known in the art, such as gapped BLAST, described in Altschul et al. Nucl. Acids Res. (1997) 25:3389-3402.

The subject nucleic acids can be cDNAs or genomic DNAs, as well as fragments thereof, particularly fragments that encode a biologically active polypeptide and/or are useful in the methods disclosed herein (e.g., in diagnosis, as a unique identifier of a differentially expressed gene of interest, etc.). The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a polypeptide of the invention.

A genomic sequence of interest comprises the nucleic acid present between the initiation codon and the stop codon, as defined in the listed sequences, including all of the introns that are normally present in a native chromosome. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at the 5' and/or 3' end of the transcribed region. The genomic DNA can be isolated as a fragment of 100 kbp or smaller; and substantially free of flanking chromosomal sequence. The genomic DNA flanking the coding region, either 3' and 5', or internal regulatory sequences as sometimes found in introns, contains sequences required for proper tissue, stage-specific, or disease-state specific expression.

The nucleic acid compositions of the subject invention can encode all or a part of the subject polypeptides. Double or single stranded fragments can be obtained from the DNA sequence by chemically synthesizing oligonucleotides in accordance with conventional methods, by restriction enzyme digestion, by PCR amplification, etc. Isolated nucleic acids and nucleic acid fragments of the invention comprise at least about 18, about 50, about 100, to about 500 contiguous nt of the sequence encoding the subject polypeptides. For the most part, fragments will be of at least 18 nt, usually at least 25 nt, and up to at least about 50 contiguous nt in length or more.

Probes specific to the nucleic acid of the invention can be generated using the nucleic acid sequences. The probes are preferably at least about 18 nt, 25nt or more of the corresponding contiguous sequence. The probes can be synthesized chemically or can be generated from longer nucleic acids using restriction enzymes. The probes can be labeled, for example, with a radioactive, biotinylated, or fluorescent tag. Preferably, probes are designed based upon an identifying sequence of one of the provided sequences. More preferably, probes are designed based on a contiguous sequence of one of the subject nucleic acids that remain unmasked following application of a masking program for masking low complexity (e.g., BLASTX) to the sequence, i.e., one would select an unmasked region, as indicated by the nucleic acids outside the poly-n stretches of the masked sequence produced by the masking program.

The nucleic acids of the subject invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

Antibodies Specific for TXR1 Polypeptides

The present invention provides antibodies specific for TXR1 polypeptides, e.g., any one of the variants, polypeptides, or domains described above. Such antibodies are useful, for example, in methods of detecting the presence of TXR1 in a biological sample, in methods of isolating TXR1 from a biological sample, and/or as a pharmaceutical agent. Such antibodies may be prepared using any convenient protocol, e.g., as described above.

Genetically altered Cell or Animal Models for TXR1 Function

The subject nucleic acids can be used to generate transgenic animals or site specific gene modifications in cell lines. Transgenic animals may be made through homologous recombination, where the normal TXR1 locus is altered. Alternatively, a nucleic acid construct is randomly integrated into the genome. Vectors for stable integration include plasmids, retroviruses and other animal viruses, YACs, and the like.

The modified cells or animals are useful in the study of TXR1 function and regulation. For example, a series of small deletions and/or substitutions may be made in the TXR1 gene to determine the role of different residues in receptor binding, signal transduction, etc. Of interest is the use of TXR1 to construct transgenic animal models for stress related disorders, where expression of TXR1 is specifically reduced or absent. Specific constructs of interest include anti-sense TXR1, which will block TXR1 expression and expression of dominant negative TXR1 mutations. A detectable marker, such as lac Z may be introduced into the TXR1 locus, where up-regulation of TXR1 expression will result in an easily detected change in phenotype.

One may also provide for expression of the TXR1 gene or variants thereof in cells or tissues where it is not normally expressed or at abnormal times of development. By providing expression of TXR1 protein in cells in which it is not normally produced, one can induce changes in cell behavior, e.g. in the control of lactation, vasodilation, etc.

DNA constructs for homologous recombination will comprise at least a portion of the TXR1 gene with the desired genetic modification, and will include regions of homology to the target locus. The regions of homology may include coding regions, or may utilize intron and/or genomic sequence. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) Methods in Enzymology 185:527-537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in culture. The transgenic animals may be any non-human mammal, such as laboratory animals, domestic animals, etc. The transgenic animals may be used in functional studies, drug screening, etc., to determine the effect of a candidate drug.

Methods of Identifying Genes Involved in Resistance to Chemotherapeutic Agents

Also provided are methods of identifying genes that are involved in resistance to chemotherapeutic agents. In these methods, as exemplified below in the Experimental Section, a functional genomic approach is employed to identify genes that mediate sensitivity to a chemotherapeutic agent.

Representative functional genomic approaches that may be employed include, but are not limited to, use of libraries of: genomic concurrent disruption elements, libraries of RNAi elements, libraries of antisense EST elements; libraries of overexpression cDNA elements; etc. Representative functional genomic approaches include those described in: U.S. Pat. Nos. 5,679,523 and 6,413,776; as well as published PCT Application Nos. WO 02/070684; WO 02/092807 and WO 02/092808, and U.S. Provisional Application No. 60/539,908 and International Application No. WO 2005/074511; the disclosure of which patents and applications, and/or corresponding United States priority documents and applications, are incorporated herein by reference.

The employed nucleic acid may be present in a number of different formats or configurations, i.e., constructs. Constructs are compositions that include a distinct nucleic acid sequence inserted into a vector, where such constructs may be used for a number of different applications, including propagation, screening, genome alteration, and the like, as described in greater detail below. Constructs made up of viral and non-viral vector sequences may be prepared and used, including plasmids, as desired. The choice of vector will depend on the particular application in which the nucleic acid is to be employed. Certain vectors are useful for amplifying and making large amounts of the desired DNA sequence. Other vectors are suitable for expression in cells in culture, e.g., for use in screening assays. Still other vectors are suitable for transfer and expression in cells in a whole animal, e.g., in the production of animal models of hyperproliferative diseases. The choice of appropriate vector is well within the ability of those of ordinary skill in the art. Of interest in certain embodiments are viral vectors. A variety of viral vector delivery vehicles are known to those of skill in the art and include, but are not limited to: adenovirus, herpesvirus, lentivirus, vaccinia virus and adeno-associated virus (AAV). Many such vectors are available commercially.

To prepare the constructs, the nucleic acid of interest is inserted into a vector, typically by means of DNA ligase attachment to a cleaved restriction enzyme site in the vector. Yet another means to insert the nucleic acids into appropriate vectors is to employ one of the increasingly employed recombinase based methods for transferring nucleic acids among vectors, e.g., the Creator™ system from Clontech; the Gateway™ system from Invitrogen, etc.

In certain embodiments, each distinct nucleic acid is present in a vector in the form of an expression cassette that includes the distinct nucleic acid. By expression cassette is meant a nucleic acid that includes a distinct nucleic acid sequence operably linked to a promoter sequence, where by operably linked is meant that expression of the coding sequence is under the control of the promoter sequence.

The cellular library that is screened according to the subject methods may be produced using any convenient protocol. The nature of the cell into which the library is placed may vary. In many embodiments, the cells into which the library to be screened is introduced are eukaryotic cells, such as plant cells, insect cells, fish cells, fungal cells, mammalian cells, and the like. Where the cells are mammalian cells, mammalian cells of interest include, but are not limited to: mouse cells, rat cells, primate cells, e.g., sequentially human cells, and the like.

The library may be introduced into the target cell population using any convenient protocol. For example, the constructs may be introduced by retroviral infection, electroporation, fusion, polybrene, lipofection, calcium phosphate precipitated DNA, or other conventional techniques. Particularly, the construct is introduced by viral infection for largely random integration of the construct in the genome. The construct is introduced into cells by any of the methods described above.

The cells of the resultant cellular library, e.g., produced as described above, are then assayed or screened for a cell phenotype of interest, e.g., a cell phenotype distinguishable from the wild-type phenotype, such as resistance to a given chemotherapeutic agent. Different types of phenotypes may include changes in growth pattern and requirements, sensitivity or resistance to infectious agents or chemical substances, changes in the ability to differentiate or nature of the differentiation, changes in morphology, changes in response to changes in the environment, e.g., physical changes or chemical changes, changes in response to genetic modifications, and the like. In representative embodiments, the change in cell phenotype is a change from resistance to a given chemotherapeutic agent to susceptibility to that agent. The cells may be screened by any convenient assay.

After identifying a cell in the library having a change in phenotype of interest and ascribing the change to the introduced nucleic acid library member therein, such as the region knocked out, turned on or silenced by the element encoded by the library member present in the cell, the modulated region may be characterized as desired, e.g., the region may be sequenced, the coding region may be used in the sense direction and a polypeptide sequence obtained. The resulting peptide may then be used for the production of antibodies to isolate the particular protein. Also, the peptide may be sequenced and the peptide sequence compared with known peptide sequences to determine any homologies with other known polypeptides. Various techniques may be used for identification of the gene at the locus and the protein expressed by the gene, since the subject methodology provides for a marker at the locus, obtaining a sequence which can be used as a probe and, in some instances, for expression of a protein fragment for production of antibodies. If desired the protein may be prepared and purified for further characterization.

The above described protocol finds use in the identification of genomic coding sequences of interest that are implicated in resistance to chemotherapeutic agents. Representative chemotherapeutic agents that may be assessed to identify genes implicated in resistance thereto include, but are not limited to those specified below.

Classes of chemotherapeutic agents (antineoplastic agents) include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan™), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below in the subsection entitled "Microtubule Affecting Agents"), Mithramycin, Deoxycoformycin, Mitomycin-C, L-Asparaginase, Interferons (especially IFN-α), Etoposide, and Teniposide.

Hormones and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

In certain representative embodiments, the chemotherapeutic agent is a microtubule affecting agent (e.g., paclitaxel, a paclitaxel derivative or a paclitaxel-like compound). As used herein, a microtubule affecting agent is a compound that interferes with cellular mitosis, i.e., having an anti-mitotic effect, by affecting microtubule formation and/or action. Such agents can be, for instance, microtubule stabilizing agents or agents which disrupt microtubule formation.

Microtubule affecting agents useful in the invention are well known to those of skill in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) Science, 274:2009) estramustine, nocodazole, MAP4, and the like. Examples of such agents are also described in the scientific and patent literature, see, e.g., Bulinski (1997) J. Cell Sci. 110:3055-3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; Panda (1996) J. Biol. Chem. 271:29807-29812.

Particularly preferred agents are compounds with paclitaxel-like activity. These include, but are not limited to paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skill in the art (see, e.g., U.S. Pat. Nos: 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) Cancer Chemother. Pharmacol. 41:37-47).

The subject methods find use in assays of determining genes involved in chemotherapeutic agent resistance, where identified gene targets may find use in the development of therapeutic products, and the like.

The following examples are offered by way of illustration and not by way of limitation.

EXPERIMENTAL

I. Experimental Procedures

A. Construction of Plasmids

The gene search vector (GSV) used to identify txr1 (FIG. 1A) was modified from a previously described retroviral vector (Li & Cohen, Cell (1996) 85: 319-329). The construct includes a cassette containing a tetracycline (Tc) regulated promoter (TcRP) and an adenovirus splice acceptor (SA) site positioned in an antisense direction to, and 5' to, a promoterless neo (G418-resistance) reporter gene in the U3 region of a murine self-inactivating pHAMM backbone, allowing expression of neo from cellular promoters flanking the site of chromosomal integration. The orientation of TcRP-activated transcription is designed to alter the function of the chromosomal gene activating neo expression by generating Tc-controlled antisense RNA.

The pEGFPTxr1 plasmid was constructed by inserting a txr1 cDNA fragment into the BglII and EcoRI sites of pCMV-EGFPN1 (Clontech, Mountain View, Calif.). pLEST-Txr1HA was constructed by inserting a txr1 cDNA fragment tagged with a 3' HA-encoding sequence into the NheI site of lentivirus based vector, pLEST (Lu et al., Proc Nat'l Acad. Sci. U S A (2004)101: 17246-17251. The structures of all constructs were confirmed by analysis of restriction enzyme digestion and by DNA sequencing. A TSP-1 promoter controlled luciferase reporter construct (pTSP1.7Luc), which contains 1.7 kb upstream sequences and the first intron of TSP-1, was a gift from Dr. Susan Cohn (Yang et al., Cancer Res. (2003) 63: 6299-6310).

B. Cell Culture and Construction of GSV Mutated Library

Media and cell culture supplements were purchased from Invitrogen. Paclitaxel, vinblastine, vincristine, adriamycin, ectoposide, cyclosporin A were purchased from Sigma. Epothilone B and TSP-1 purified from human platelets were purchased from EMD Biosciences. Docetaxel (Adventis) was a gift from Dr. Branimir Sikic. TSP-1 mimetic peptides, 4N1K(KRFYVVMWKK (SEQ ID NO:01)), amino acid 1016-1023) and its control peptide 4NGG (KRFYGGM-WKK(SEQ ID NO:02)) were synthesized by GeneMed (South San Francisco, Calif.); ABT-510 (GVITRIR (SEQ ID NO:03), amino acid 553-559) was a gift from Abbott Laboratories. M2182 (Bae et al., Prostate (1998) 34: 275-282) cells were cultured in serum-free media RPMI1640 supplemented with 0.1 uM dexamethasone, 10 ng/ml epidermal growth factor, 50 µg/ml gentamycin, 5 µg/ml insulin, 5 µg/ml transferrin, and 5 ng/ml selenium. 293t cells were maintained in DMEM supplemented with 10% fetal bovine serum, 50 µg/ml streptomycin and 50 units/ml penicillin. All cells were maintained in 5% $CO_2$ humidified incubators at 37° C. M2182tTA cells were established by introducing a construct expressing the Tc-repressed transactivator (tTA) and selecting for clones showing the greatest change in expression of the luciferase reporter gene upon addition of Tc. Retrovirus was produced by co-transfection of GSV DNA with pGP (expressing gag and pol genes) and pVSVG (vesicular stomatitis virus glycoprotein for pseudo-typing the envelope protein) (Ory et al., Proc. Nat'l Acad. Sci. U S A (1996) 93:11400-11406) into 293t cells. Virus-containing media were harvested 48 hr post-transfection and co-cultured with M2182tTA cells in the presence of 8 µg/ml polybrene for 48 hr. Permanently infected clones containing a GSV insertion near a transcriptionally active region were selected by treating the infected cells with 500 µg/ml G418 for two weeks. A library containing $5 \times 10^5$ independent GSV virus insertions was constructed by pooling cells from several separate infections and used for subsequent screenings.

C. Selection of Taxol Resistant Cells and Measurement of Drug Resistance

M2182tTA cells containing GSV virus insertion libraries were seeded at a density of $5 \times 10^5$ per 10 cm plate one day prior to the addition of 10 nM taxol; preliminary experiments showed no surviving M2182tTA cells after 5 days of exposure to 5 nM taxol. After 14 days selection in the presence of taxol, visible colonies were pooled and exposed to 10 nM taxol in a second round of screening. 24 individual colonies obtained from this screening were isolated and expanded. For subsequent plate assays of the effects of taxol and other drugs on colony formation, $1 \times 10^4$ cells per 10 cm plate or per each well of six-well plate were seeded one day prior to drug treatment at the concentrations indicated. After 7 to 14 days exposure to drug, the resistant colonies were stained with 0.5% crystal violet solution and photographed. For quantitative determination of the surviving fraction, the collection of crystal violet stained colonies were incubated with 0.5 ml of DMSO overnight and the absorbance at 570 nm of dye extracted solution was measured. The fraction of surviving cells was calculated relative to non-treated controls. Results were averaged from at least two to three independent experiments. For $IC_{50}$ determination, $3 \times 10^3$ cells per well of a 96-well plate were seeded one day prior to treatment by serially diluted drugs or in combination with indicated protein/peptides. The viability of treated cells was quantified by their ability to reduce tetrazolium salt 3-(4,5-dimethylthiazol-2-y)-2,5-diphenyl tetrasodium bromide (MTT, Sigma) to a formazan dye whose absorbance is detectable at 570 nm. The $IC_{50}$ value was defined as the dose of taxol that inhibited cell growth by 50%. For TUNEL assays, $5 \times 10^4$ cells/well were seeded on circular coverslips in 24-well plates one day prior to treatment with drug in the presence or absence of 7.5 µg/ml purified TSP-1 for 3 days. Cells were then fixed with 4% paraformaldehyde for 10 min, permeabilized with 0.3% Triton X-100 for 5 min, and incubated with TdT reaction buffer (Roche Molecular Biochemicals) at 37° C. for 2 hr. The buffer was then aspirated, and the slides were incubated with TdT buffer at 37° C. for 1 hr. After mounting in antifade (Molecular Probes), slides were viewed using a confocal microscope (Leica).

D. Measurement of Taxol Uptake $1 \times 10^4$ cells were seeded in each well of 24-well plates one day prior to drug treatment. Media were removed and replaced with media containing 50 nM of [$^3$H] paclitaxel (3.2 Ci/mmol, Moravek Biochemicals). Cells were incubated with [$^3$H] paclitaxel for 3 hr, cooled on ice, washed three times with ice-cold PBS, and lysed by addition of 0.25 ml of 1% SDS. The radioactivity in each sample was determined by scintillation counting.

E. Cloning of Provirus Integration Site by PCR-Based Genomic Walking

Genomic DNA was extracted from taxol resistant cells by using the Gentra genomic DNA extraction kit (Gentra Systems). Genomic DNA flanking the GSV integration site was cloned using the GenomeWalker kit (Clontech, Mountain View, Calif.) followed by PCR amplification using Expand High Fidelity PCR Systems (Roche Applied Science). An oligonucleotide corresponding in sequence to the sense strand of the neo gene (5'-GCTGACCGCTTCCTCGTGC-TTTACGG-3')(SEQ ID NO:04) was used as primer.

F. Reverse Transcription Polymerase Chain Reaction (RT-PCR)

Poly(A) RNA was extracted from cells using the FastTrack kit (Invitrogen) and quantified by UV absorbance spectroscopy. The chained reverse transcription and Taq polymerase reactions were performed as described in the vendor's manuals. Sequences of oligonucleotides, cycle numbers used for amplification, and product size of each gene were:

β Tubulin class I:
5'-ACCTCGCTGCTCCAGCCTCT-3' (SEQ ID NO: 5)
and
5'-CCGGCCTGGATGTGCACGAT-3', (SEQ ID NO: 6)
25 cycles, 154 bp;

β Tubulin class III:
5'-ACATCTCTTCAGGCCTGACAATTTCATC-3' (SEQ ID NO: 7)
and
5'-TGCTGATGAGCAACGTGCCCATGCCGGAGC-3', (SEQ ID NO: 8)
25 cycles, 220 bp;

Txr1:
5'-ATGGTTGGACCAGCAGTGATA-3' (SEQ ID NO: 9)
and
5'-GGAAGGGTCCAGGGCCTGTAT-3', (SEQ ID NO: 10)
20 cycles, 156 bp.

G. Antibodies and Immunoblotting

A peptide, N15 (AGQPGPNPYPPNIGC (SEQ ID NO:11), a.a. $6^{th}$ to $20^{th}$, FIG. 2B), corresponding to a segment of Txr1 was synthesized and used as antigen for raising rabbit polyclonal antibodies by Covance. Anti-α-tubulin monoclonal antibody was purchased from Sigma and anti-TSP-1 monoclonal antibody was purchased from Lab Vision. For immunoblotting, 15 µg (for Txr1) or 30 µg (for TSP-1) of cell lysates were separated by 15% or 4-20% SDS-PAGE (Bio-Rad), blotted onto Nitrobind nitrocellulose (Osmonics), and probed with antibody (1:2000 dilution for anti-Txr1, 1:5000 dilution for anti-α-tubulin, and 1:250 dilution for anti-TSP-1). Signals were detected by Western Lightning reagent (PerkinElmer).

H. Immunofluorescence Staining

Experiments were carried out as described previously (Xie et al., (Proc. Nat'l Acad. Sci. U S A (1998) 95:1595-1600). Briefly, cells were fixed, permeabilized, blocked and incubated with either primary antibody or preimmune serum (1:250 dilution), and then with secondary antibody conjugated with the fluorescent dyes Oregon Green 488 (1:500 dilution, Molecular Probes). For localization of GFP-fusion protein, cells transfected with a GFP-expressing construct alone or with fusion constructs were fixed with 4% paraformaldehyde for 10 min and stained with DAPI for 10 min. Fluorescent images were obtained by using a confocal microscope (Leica).

I. Northern Blot and Microarray Hybridization

Poly(A)-RNA was separated by formaldehyde/MOPS 1% agarose gel, transferred onto Hybond-N nylon membrane (Amersham Biosciences), and hybridized with radioactively labeled cDNA fragments according to the vendor's instruction manual. Multiple-tissue blots were purchased from Clontech (Mountain View, Calif.). cDNA microarrays on glass slides, which contained approximately 42,000 sequence-verified IMAGE clones representing ~28,000 different genes, were made essentially as described (Eisen & Brown, Methods Enzymol. (1999) 303: 179-205). Detailed protocols are available at the website having an address made up of "http:" placed in from of "//cmgm.stanford.edu/pbrown/array.html". 2 µg of poly(A)-RNA were labeled by reverse transcription using SuperScript II enzyme (Invitrogen) and oligo(dT)$_{18}$ primer (New England BioLabs) in the presence of Cy3-dUTP or Cy5-dUTP (Amersham Pharmacia). Slides were hybridized for about 16 hr in a 65° C. water bath and scanned at 10 µm resolution with a GENEPIX 4000B scanner (Axon Instruments). Data were processed and analyzed by GABRIEL as described previously (Pan et al., Proc. Nat'l Acad. Sci. U S A (2002) 99: 2118-2123; and Zhang et al., Proc. Nat'l Acad. Sci. U S A (2003) 100: 3251-3256). Briefly, a pattern based rule that selects genes showing reduced or elevated expression in clone 18 in the absence of Tc but similar expression as the parental cell line in the presence of Tc was employed. Thresholds used to define "elevated" or "reduced" were determined by yielding false discovery rate (FDR) values less than 0.001.

J. Promoter Activity Analysis $2 \times 10^5$ cells were plated in 6-well dishes for 24 hr prior to transfection. 2 µg of TSP-1 promoter luciferase report construct was transfected into cells with 0.2 µg of pCMVlacZ (as an internal control to monitor transfection efficiency) by FuGENE 6 (Roche Applied Science). Cell lysates harvested at 48 hr after transfection were used to measure luciferase activity by luciferase assay kit (Promega) according to manufacturer's instruction and to determine β-galactosidase by gal reporter chemiluminescent assay (Roche Applied Science). Relative luciferase units were calculated by normalizing the luciferase activity with β-galactosidase activity.

K. NCI-60 Data Analysis

For NCI-60 data analysis, drug activity data (A-matrix) were downloaded from the website having an address made up of "http:" placed before "//discover.nci.nih.gov/datasetsNature2000.jsp", and gene expression data were downloaded from the website having an address made up of "http:" placed before "//genome-www5.stanford.edu/cgi-bin/publication/viewPublication.pl?pub_no=81". Selection of genes that passed the data quality filter resulted in nineteen cell-lines whose data points for Txr1 (gene name: DKFZP51J157) and TSP-1 (THBS) gene expression were available. The Pearson correlation coefficient of taxol sensitivity with expression of Txr1 and TSP-1 was determined by the mean center method as described in (Pan et al., 2002, supra) for 13 of these 19 lines that showed reciprocally altered expression of Txr1 and TSP-1.

L. siRNA Mediated Knockdown of Gene Expression

Two siRNA duplexes corresponding to segments of txr1 mRNA (accession number: AF217517), SI1 ($80^{th}$-$102^{nd}$, 5'-AAGAGCGAGACUGCGAAGGAGAdTdT-3' (SEQ ID NO:12) and 5'-UCUCCUUCGCAGUCUCGGCUCdTdT (SEQ ID NO:13) and SI2 ($761^{st}$-$783^{rd}$ 5'-AAGAGGAUUGCCAUGGCCUGGCCdTdT-3' (SEQ ID NO:14) and 5'-GGCCAGGCCAUGGCAAUCCUCdTdT-3'(SEQ ID NO:15), and a pre-synthesized scrambled sequence control (non-specific Control Duplex VIII) were purchased from Dharmacon. An siRNA duplex against TSP-1 was purchased from Santa Cruz Biotechnology (sc# 29528). $2 \times 10^5$ cells were plated in six-well dishes one day prior to transfection of cells with 50 nM siRNA oligo nucleotides using DharmaFECT (Dharmacon). 48 hr later, transfected cells were analyzed for taxol resistance by colony formation assay or MTT assay.

M. Flow Cytometry Analysis $2 \times 10^5$ cells were plated in 60 mm dishes one day prior to analysis. Cells were detached by 10 mM EDTA, washed with cold PBS with 1% fetal bovine serum, incubated 30 min on ice with either fluorescein isothiocyanate conjugated anti-CD36 monoclonal antibody (1:20 dilution, clone FA6.152, Beckman), phycoerythrin conjugated anti-CD47 monoclonal antibody (1:20 dilution, clone B6H12, BD Pharmingen) or corresponding isotype antibody (mouse IgM for anti-CD36, mouse IgG for anti-CD47) at the same dilution. Flow cytometry was performed with FACScan (Becton Dickinson) and the results analyzed using FlowJo software. Experiments were done three times with similar results.

II. Results

A. Isolation of Taxol Resistant Clones

Identification of cells acquiring resistance to taxol employed the overall experimental approach described by Li and Cohen (Li and Cohen, 1996, supra) with two major modifications in the gene search vector (GSV) (FIG. 1A)—substitution of neo for β-geo as reporter to reduce the size of vector and consequently increase virus production, and use of a tetracycline-controlled promoter (TcRP) to produce antisense transcripts that inhibit the expression of chromosomal genes. A human prostate cancer cell-line, M2182, which was found in initial experiments to be highly sensitive to infection by our retroviral GSV construct, was transfected with the Tc-off transactivator gene (tTA) to generate a Tc-responsive clone (M2182tTA) that subsequently was targeted for infection by the GSV. A pool of M2182tTA cells containing a total of $5 \times 10^5$ independent GSV retroviral insertions was exposed to 10 nM taxol for two sequential two-week cycles of screening. Three clones (clones 4, 14, and 18) that formed prominent colonies at this taxol concentration were further characterized by MTT assay to determine the $IC_{50}$ (FIG. 1B). Clone 18, which had a growth rate similar to that of parental M2182tTA cells but showed an $IC_{50}$ approximately two and a half-fold greater than the $IC_{50}$ of the parental cells (FIG. 1B and Table 1), was chosen for further study; clones 4 and 14 produced smaller colonies when cultured in 10 nM taxol and showed a lesser increase in $IC_{50}$ (FIG. 1B). Addition of 1 μg/ml Tc to cultures of clone 18 reversed its ability to grow in the presence of either 10 nM taxol or 2 nM docetaxel, a more potent taxane (FIG. 1C). The absence of detectable effects of Tc on the size or density of colonies in the absence of taxanes indicated that the taxol resistance observed for clone 18 was being regulated by the TcRP promoter.

No evidence of reduced killing of clone 18 cells by the DNA damaging agents adriamycin and etoposide, by the microtubule destabilizing agents vincristine and vinblastine, or by the microtubule stabilizing drug epothilone B, suggesting that the taxol resistance observed in this clone does not result from multi drug resistance (MDR) (Table 1). Consistent with this conclusion was evidence that 2 μM cyclosporin A, a MDR inhibitor that has been reported to reverse the cellular effects of MDR did not affect taxol resistance (data not shown). Moreover, whereas down-regulation of the TcRP promoter in the chromosomally inserted GSV of clone 18 cells decreased taxane resistance (FIG. 1C), it had no effect on the intracellular accumulation of [$^3$H] taxol (FIG. 1D). Clone 18 cells also showed no indication of altered expression of β-tubulin class I and III microtubule proteins, which commonly are elevated in taxol resistance due to altered microtubule function (Kavallaris et al., 1997), (FIG. 1E). Collectively, these findings indicated that the taxol resistance observed in clone 18 does not result from either of these previously studied mechanisms.

TABLE 1

Drug sensitivity of M2182tTA and Clone 18

| Chemotherapy agents (unit) | $IC_{50}$[a] | | Fold of resistance[b] (Clone 18/M2182tTA) |
|---|---|---|---|
| | M2182tTA | Clone 18 | |
| Adriamycin (ng/ml) | 150.1 ± 9.9 | 133.33 ± 7.1 | 0.83 |
| Etoposide (uM) | 0.8 ± 0.03 | 0.65 ± 0.06 | 0.81 |
| Vinblastine (nM) | 7.5 ± 0.18 | 7.0 ± 0.21 | 0.93 |
| Vincristine (nM) | 11.5 ± 0.78 | 12 ± 0.42 | 1.09 |
| Epothilone B (nM) | 0.75 ± 0.35 | 0.68 ± 0.21 | 0.9 |
| Taxol (nM) | 7.2 ± 0.11 | 17.5 ± 0.18 | 2.45 |
| Docetaxel (nM) | 2.66 ± 0.11 | 6.93 ± 0.05 | 2.62 |

[a]Drug sensitivities were analyzed by the MTT assay as described in Experimental Procedures. $IC_{50}$ is the drug concentration that inhibited cell survival by 50%. Values are the means ± SD of three independent determinations having quadruple repeats in each.
[b]Fold of resistance was calculated by dividing $IC_{50}$ of clone 18 divided with $IC_{50}$ of M2182tTA.

B. Identification and Characterization of Txr1

Southern blot analysis of genomic DNA from clone 18 cells indicated that the proviral form of the GSV had integrated into a single chromosomal site (data not shown). Genomic DNA fragments flanking this site were cloned using a PCR-based genome walking method as described in Experimental Procedures, and the sequences of PCR products were determined and analyzed by the BLAT program (http://genome.ucsc.edu). This analysis indicated that the GSV was inserted into a locus on chromosome 12 (region 12q13.13) at a position 499 bp 5' to a putative gene of unknown function that previously has been identified from expressed sequence tags (ESTs) (GeneID: 54458, symbol: DKFZp564J157). The longest EST reported from this locus, which consists of four putative exons and extends for about 5 kb (FIG. 2A), is 1189 base pairs in length (accession number: BC001464). We designated the locus as txr1 (taxol resistance gene 1). Comparison of EST sequences corresponding to the txr1 locus revealed at least three transcriptional variants: variant 1 (NM_001005355), variant 2 (NM_018457), and variant 3 (NM_001005354). While variants 1 and 2 both contain a deletion in the 5' UTR and encode an open reading frame (NP_001005355) whose sequence corresponds to a 148 amino acid protein of 15,243 Daltons (FIG. 2B) (SEQ ID NO:16), variant 3 contains deletions in part of the sequence of the 5'UTR and the ORF and encodes an isoform (NP_001005354) lacking the coding sequence for the first 56 amino acids.

The amino acid composition of the protein predicted from analysis of the txr1 locus is noteworthy. The longest predicted gene product (Txr1) contains 44 proline residues (29.7% of entire protein) in the first 101 amino acids, eight histidines and thirteen lysines in the C-terminal 48 amino acid segment, and remarkably, a continuous stretch of 10 serine residues at the C-terminus (FIG. 2B). Further analysis revealed several putative α helix motifs in the first 100 amino acids of the protein and putative βsheet structures near the C terminal end. Spatial alignment of prolines in Txr1 with prolines in other proteins having biological functions that include SH3/WW domain binding, RNA binding, and cell mobility—but no homology with other proteins in inter-proline spaces—was observed.

Northern blot analysis of total RNA isolated from clone 18 detected a single txr1 transcript species migrating in agarose gels at 1.2 kb, which corresponds in length to the EST variant 1. This transcript species was upregulated five-fold in clone 18—and in the presence of Tc was reduced to the level found in the parental cell line (FIG. 2C, upper panel). Increased txr1 transcription in clone 18 was confirmed by RT-PCR analysis (FIG. 2C, lower panel). Immunoblotting experiments (FIG. 2B) showed that the abundance of an 18 kDa species corresponding in size to the predicted full length Txr1 protein was five-fold higher in clone 18 than in parental cells and that its upregulation was reversed by Tc (FIG. 2D). Immunofluorescence staining using anti-Txr1 antibody and direct visualization of a Txr1-GFP fusion protein both showed that Txr1 is localized predominantly in the nucleus (FIG. 2E). Multiple-tissue Northern blotting indicated that txr1 transcripts are broadly expressed and are especially prominent in heart, kidney and leukocytes (FIG. 2F).

Figure 3:
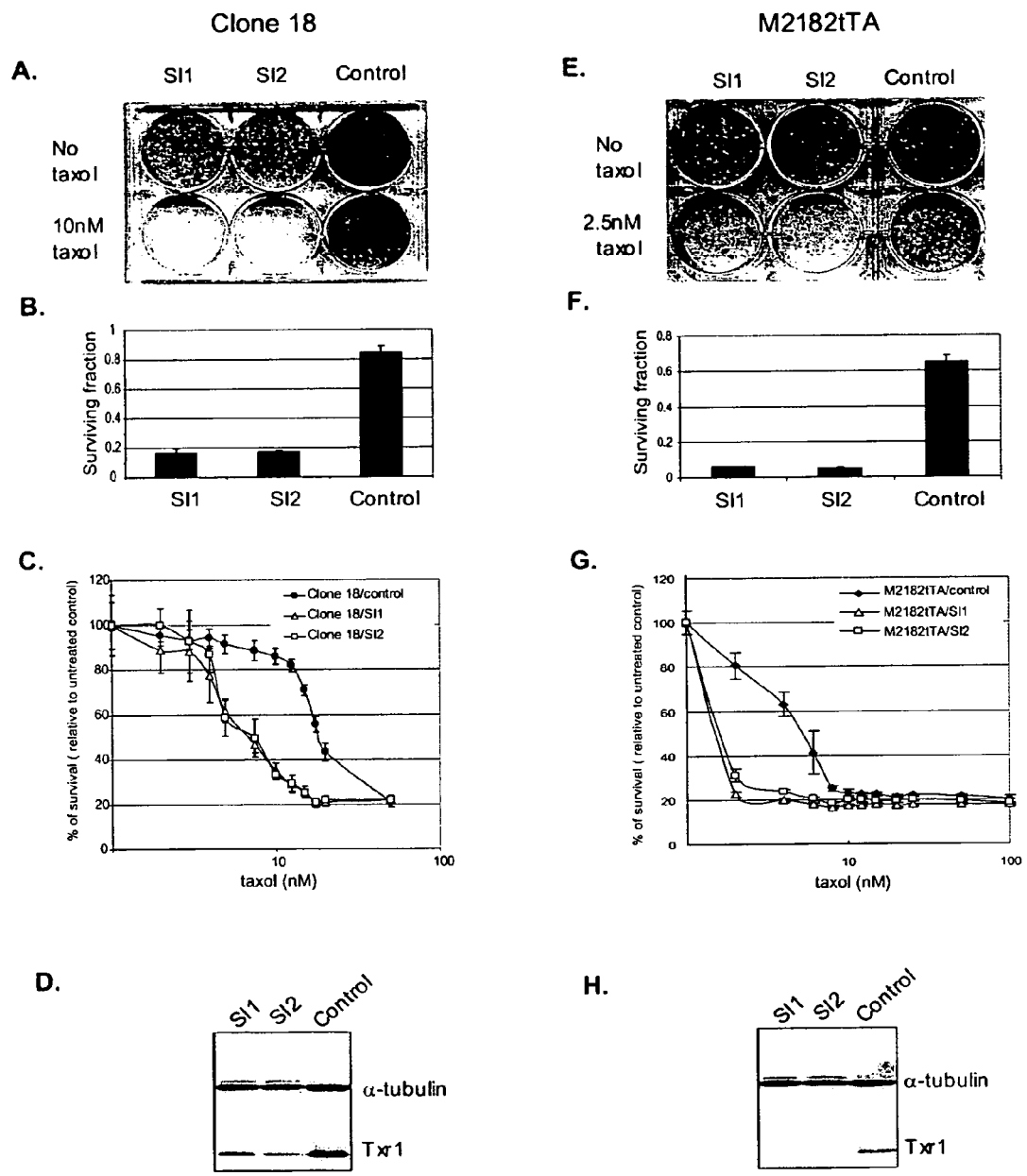
FIGS. 3A to 3H. Downregulation of txr1 by siRNA Reduces the Taxol Resistance of Clone 18 (FIGS. 3A-3D) and Increases Taxol Sensitivity of Naïve M2182tTA Cells (FIGS. 3E-3H) (FIG. 3A) and (FIG. 3E) Immunoblotting analysis effects of siRNA on Txr1 protein abundance. Clone 18 (FIG. 3A) and M2182tTA cells (FIG. 3E) were transfected with siRNA (SI1 and SI2) against txr1 and with a scrambled-sequence control, cell lysates harvested 48 hr after transfection were subjected to immunoblotting analysis and probed with anti-Txr1 and anti-α-tubulin antibodies.
Figure 5:
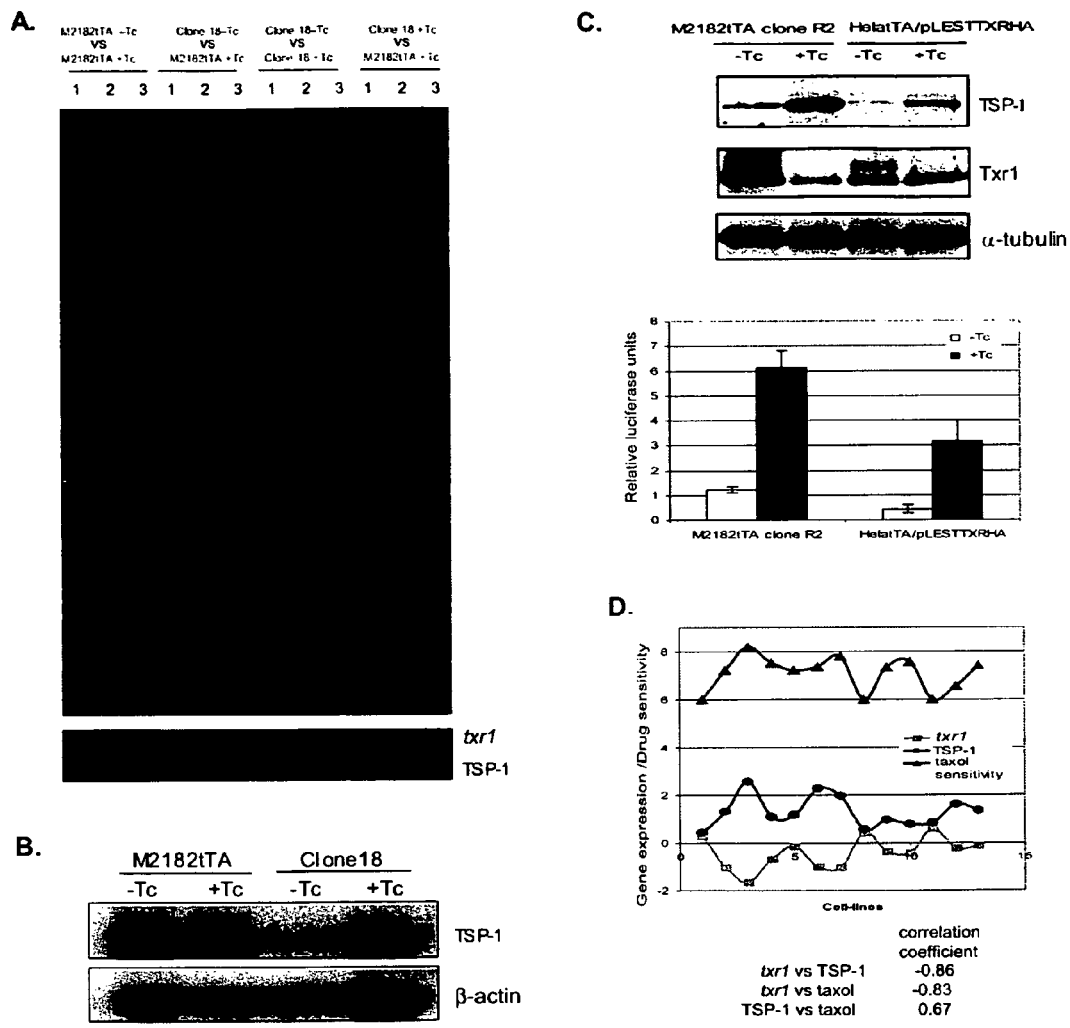
FIGS. 5A to 5D. Effect of Txr1 on Transcription of TSP-1 (FIG. 5A) Graphic representation of global effects of Txr1 upregulation on transcription as measured by cDNA microarray hybridization. cDNA corresponding to mRNA extracted from indicated cells/conditions was labeled with Cy5 (typed in red) or Cy3 (typed in green) for competitive hybridization on microarrays. Three independent hybridizations were performed for each pair of comparison. Color represents the direction of regulation in gene expression: green-decreased expression, red-increased expression and black-unchanged. Color saturation is proportional to the magnitude of the change in relative expression. The gene list is provided in Supplemental Data. The expression profiles for Txr1 and TSP-1 are displayed in lower panel.

C. Txr1 Upregulation is Necessary for the Taxane Resistance of Clone 18 and is Sufficient to Induce Cellular Resistance to Taxanes in Naïve Cells We further confirmed the role of Txr1 in the taxol resistance of clone 18, and—in experiments that used two small interfering RNAs (siRNA1 and 2) complementary to the 5' and 3' untranslated regions of txr1 to reduce expression of the gene—showed that upregulation of Txr1 is necessary for this resistance. Clone 18 cells that were transiently transfected with siRNAs against txr1 or with a scrambled siRNA sequence as a control showed a 75% to 80% decrease in cell survival in the presence of 10 nM taxol (FIGS. 3A, 3B, and 3C) and a concomitant reduction in steady state level of Txr1 protein as assessed by immunoblotting (FIG. 3D). Similarly, treatment of naïve M2182tTA cells with siRNAs directed against txr1 resulted in decreased survival in the presence of taxol (FIGS. 3E, 3F, 3G, and 3H), but no difference in sensitivity to the non-taxane chemotherapeutic drugs adriamycin, etoposide, vinblastine, vincristine, and epothilone B (data not shown). We were unable to isolate cells that stably expressed Txr1 from the CMV promoter. However, infection of M2182tTA cells with the lentiviral construct pLEST-Txr1HA, which uses the TcRP promoter to express Txr-1 protein tagged with HA, and selection for continued cell growth in the presence of Tc led to the isolation of two clones (R1 and R2) that stably express Txr-1. These clones showed induction of Txr1 expression in the absence Tc (three-fold in R1 and 2.5-fold in R2, FIG. 4A) and increased survival during exposure to a taxol concentration of 2.5 to 4 nM (FIGS. 4B, 4C, 4D, and 4E), confirming the role of txr1 in taxol resistance D. Role of Thrombospondin-1 as a Regulator of Cellular Sensitivity to Taxol In initial experiments aimed at elucidating the mechanism underlying the taxane resistance observed in cells overexpressing Txr1, cDNA microarrays were used to compare the gene expression profiles for clone 18 and M2182tTA cells in the presence or absence of Tc. The resulting data, which was analyzed using the GABRIEL system of rule-based computer programs (Pan et al., 2002, supra), identified 59 upregulated genes (FDR<0.001) and 49 downregulated genes (FDR=0.001) showing Tc-controlled differential expression (FIG. 5A, see gene list in Supplemental Data). Not surprisingly, txr1 itself was the most upregulated gene (6.8±1.0 fold), consistent with the prominently increased mRNA abundance we had detected by Northern blotting and RT-PCR (FIG. 2C). The most downregulated transcript among the ~28,000, analyzed on microarrays was encoded by thrombospondin-1 (TSP-1, 3.65±0.8 fold) (FIG. 5A, lower panel), an extensively studied gene that has both pro-apoptotic and anti-angiogenic activities. Analysis of the gene expression data in FIG. 5A using the proband-based rule of GABRIEL showed a dramatically negative Pearson correlation coefficient (r) of −0.92 between txr1 and TSP-1. Northern blotting confirmed that TSP-1 RNA abundance was sharply decreased in clone 18 when Tc was lacking from the media (i.e., during induction of Txr1 expression in this clone), and that expression of TSP-1 in the parental cell line was unaffected by Tc (FIG. 5B, upper panel).

To further explore the mechanism of Txr1 mediated TSP-1 downregulation, we examined the effects of Txr1 on TSP-1 transcription using firefly luciferase cDNA fused to the TSP-1 promoter region as a reporter (FIG. 5C). In a Tc-regulated Txr1-expressing M2182-derived clone (i.e., R2, FIG. 4) and in a HeLa cell-derived clone in which we adventitiously expressed Txr1 under the control of the TcRP promoter, addition of Tc resulted in a five- to six-fold increase in TSP-1 protein abundance (FIG. 5C, upper panel) accompanied by a similar increase in luciferase activity (FIG. 5C, lower panel), indicating that Txr1 negatively regulates TSP-1 expression at the level of transcription initiation.

Analysis of a previously published gene expression dataset for NCI-60 cancer cell-lines (Scherf et al., Nat. Genet. (2000) 24: 236-244) indicated that expression of Txr1 and TSP-1 was regulated reciprocally (r=−0.83) in 13 of 19 cell lines for which expression data were available for both genes. Among these 13 lines, the extent of cellular sensitivity to taxol showed a prominent negative correlation with the steady-state level of expression of txr1 (r=−0.86) and a positive correlation with TSP-1 (r=0.67) (FIG. 5D). These results argue that reciprocal expression of Txr1 and TSP-1 occurs commonly among cancer cell-lines and that the level of expression of these two genes is correlated with the extent of cellular sensitivity to taxol in multiple cancer cell types.

The effect of TSP-1, which normally is secreted and exists as an extracellular protein (Sid et al., Crit. Rev. Oncol. Hematol. (2004) 49: 245-258) was directed examined on taxane sensitivity by adding purified TSP-1 to clone 18 cells growing in culture. TSP-1 addition to the media was observed to result in dose-dependent partial reversal of the taxol resistance of clone 18 (FIG. 6A); however, no effects of TSP-1 on killing of clone 18 cells by other chemotherapeutic agents we tested were observed (FIG. 6C), indicating that the drug-potentiating effects of TSP-1 in clone 18 cells are specific to taxane. Addition of TSP-1 to cultures of naïve M2182tTA cells also reduced survival to taxol-mediated lethality (FIG. 6B), and again, TSP-1 sensitization was not observed for the other chemotherapeutic drugs we tested (FIG. 6D).

Whereas TSP-1 itself had only limited ability to reduce survival and induce apoptosis at the dosage added to cultures of clone 18 cells in the above experiments, (FIGS. 6B, C, and D), it dramatically and synergistically increased taxol-induced apoptosis, as determined by TUNEL assay (FIG. 6E). Conversely, decreasing the expression of endogenous TSP-1 to 30% of the control level (FIG. 6F) by treatment of naïve M2182 cells with siRNA directed against TSP-1 transcripts resulted in survival at a taxol concentration (3 nM) that was lethal to an identical cell population transfected with control siRNA having a randomly scrambled sequence (FIG. 6G). Lethality of other chemotherapeutic drugs in M2182 cells was unchanged by reduction of TSP-1 expression (data not shown).

1. E. Sensitization to Taxanes is Mediated Through Interaction of TSP-1 with CD47 Receptors on the Cell Surface The results presented above indicate that Txr1 transcriptionally downregulates expression of TSP-1, that such downregulation can modulate taxane-induced apoptosis, and that exposure of taxane-resistant prostate cancer cells to TSP-1 in culture can increase the lethality of taxanes without affecting the actions of other chemotherapeutic agents in these cells.

We wished to understand the basis for this taxane-related specificity. Earlier work has shown that the widely studied anti-angiogenic effects of TSP-1 result from its ability to promote apoptosis of endothelial cells through signaling pathways initiated by its interaction with CD36 receptors on the cell surface. TSP-1 can also regulate cell adhesion and migration through its interaction with a different receptor, CD47, also known as integrin-associated protein (IAP). During flow cytometry experiments that analyzed clone 18 and M2182tTA cells for expression of each of these recpetors, we detected only CD47 (FIG. 7A)—leading us to hypothesize that this receptor protein may be implicated in the modulation of taxane resistance by TSP-1. To determine the correctness of this notion, we examined the ability of the CD47 agonist peptide 4N1K, which corresponds to a sequence (amino acid residues 1016 to 1023) near the C-terminal end of TSP-1, to affect taxane resistance; this peptide has been shown to bind highly specifically to CD47 and to actions on CD47-mediated signaling of cell migration that are similar to those of the full length TSP-1 protein. 4NGG, a non-active variant of the 4N1K peptide, and ABT-510, a CD36 agonist peptide, were used as controls. As seen in FIG. 7B, exposure of clone 18 cells to 4N1K resulted in dose-dependent partial reversal of the taxol resistance induced by overexpression of Txr1 in clone 18 (FIG. 7B, left upper panel), whereas the same concentration of peptide 4NGG or ABT510 had no effect on taxol cytotoxicity (FIG. 7B, left middle and lower panels). Similarly, as we observed for the full length TSP-1 protein, addition of 4N1K, but not of 4NGG or ABT-510, to M2182tTA naïve cells growing in culture enhanced cell killing by taxol (FIG. 7B, right panels), further implicating CD47 in TSP-1 modulation of taxane cytotoxicity. Whereas CD47-mediated signaling by the 4N1K peptide had no detectable effects on the sensitivity of M2182tTA or clone 18 cells to other chemotherapeutic agents we tested (FIG. 7C), TSP-1 interaction with the CD36 receptor recently has been reported to enhance the killing of endothelial cells by adriamycin (Quesada et al., Cell Death Differ. (2005)).

The above results indicate that CD47-mediated signalling by TSP-1 is sufficient to enhance the cytotoxicity of taxanes. Additional experiments that were carried out using an antibody that interferes with the functioning of CD47 (i.e. B6H12, (Blystone et al., J. Cell Biol. (1994) 127: 1129-1137; Gao et al., J. Cell Biol. (1996a) 135: 533-544; and Gao et al., J. Biol. Chem (1996b) 271: 21-24) show that in the cell lines that were studied, CD47 is also necessary for such enhancement. In these studies, the addition of anti-CD47 antibody resulted in a 2.2-fold increase in viability of M2182tTA cells to taxol treatment (FIG. 7D, left panel). An increase in cells that survive taxol treatment was also observed during exposure of these cells to pertussus toxin, which uncouples the heterotrimeric inhibitory G protein, Gi from CD47 and interrupts CD47-mediated signaling (Moss and Vaughan, 1988), (FIG. 7D, center panel). Consistent with these observations, the ability of the 4N1K peptide to reverse taxol resistance in clone 18 cancer cells also depended on the function of CD47, as anti-CD47 antibody abrogated this effect (FIG. 7D, middle panel). Collectively, these experiments indicate that regulation of taxane cytotoxicity by TSP-1 is dependent on CD47-mediated signaling in the cells that were studied.

III. Discussion

A. Role of txr1 Taxane-Induced Cytotoxicity and TSP-1 Expression

The results reported here reveal the existence of a novel mechanism that both regulates expression of the pro-apoptotic, anti-angiogenic protein, thrombospondin-1 and modulates cellular cytotoxicity by taxanes. Increased expression of a gene of previously unknown function, here designated as txr1, confers resistance to taxanes at least in part by transcriptionally downregulating TSP-1, and consequently reducing taxane-mediated apoptosis in human cancer cells. The effects of the txr1/TSP-1 pathway are distinct from previously elucidated mechanisms of taxol resistance and are dependent on the ability of a C-terminal peptide domain of TSP-1 to activate signaling mediated by the CD47 integrin associated protein on the surface of the tumor cells we studied.

The function-based screening approach used to identify txr1 was designed to discover human genes whose homozygous inactivation by antisense RNA initiated from a Tc-controlled retrovirus-borne chromosomally inserted promoter results in a phenotype of interest (Li and Cohen, 1996). However, the analysis of the DNA region containing the GSV inserted into the chromosome of clone 18 indicated that the predicted transcriptional start site of the txr1 gene is located about 0.5 kb 3' to the GSV insertion site, and subsequent analysis of txr1 expression indicated that taxane resistance resulted from Tc-dependent activation, rather than downregulation, of txr1. We speculate that such upregulation of txr1 expression is a consequence of insertion of the Tc-dependent enhancer segment of the TcRP promoter near the gene's transcription start site.

The causal role of txr1 in determining the taxane resistance observed in clone 18 was suggested initially by the concurrent regulation of Txr1 expression and taxol resistance by the GSV-borne promoter inserted at txr1 and by the effects of siRNA directed against txr1 transcripts in this cell clone. This role was confirmed by evidence that elevation of the steady-state level of Txr1 protein in naïve cells recapitulated the taxane resistance phenotype and the ability of siRNA against txr1 to increase cellular sensitivity to taxol. We subsequently found that increased Txr1 expression was accompanied by reciprocal downregulation of TSP-1 and a concomitant decrease in taxol-mediated apoptosis.

B. Actions of TSP-1 in Determining Cellular Sensitivity to Taxanes

Although the functions of TSP-1 have been widely studied, its role in determining cellular sensitivity to taxanes previously has not been known. During our investigations, we observed decreased Txr1-dependent TSP-1 promoter activity, transcript abundance, and protein production—revealing Txr1 as a negative regulator of TSP-1 expression. We further found that resistance to taxol-induced cytotoxicity is reversed by addition of purified TSP-1 or the TSP-1 mimetic peptide 4N1K to cultures of clone 18 cells, that sensitivity to taxane cytotoxicity is enhanced by TSP-1 or 4N1K in naïve cells, that the actions of TSP-1 and taxanes are synergistic in the killing of cancer cells, and that Txr1 upregulation and TSP-1 downregulation were highly correlated with reduced taxol sensitivity in 13 of 19 NCI-60 human cancer cell lines. Additionally, we found that antibody directed against the CD47 receptor interfered with the ability of TSP-1 and 4N1K to enhance taxane sensitivity. Together these findings demonstrate a mechanistic role of TSP-1 in mediating the effects of Txr1—and more generally, in modulating the effectiveness of taxol in the killing of cancer cells.

TSP-1 is an extracellular-matrix-bound adhesive glycoprotein that earlier was found to suppress tumorgenicity, cancer progression, and tumor metastasis by inhibiting endothelial cell proliferation and consequently, the angiogenesis required to supply growing cancers with oxygen and nutrients. TSP-1 expression is known to be downregulated by the Id1 transcription factor and a variety of oncogenes. The results reported here indicate Txr1 is also among the down-regulators of TSP-1.

The anti-angiogenic actions of TSP-1, which occur through its interaction with the CD36 receptor on the surface of endothelial cells, are mimicked by the ABT-510 peptide, which interacts specifically with this receptor. These anti-angiogenic effects have been reported to be synergistic with the anti-tumor actions of chemotherapeutic agents, leading to a slowing of cancer progression in mice. Additionally, TSP-1 itself and the CD36-binding ABT-510 peptide which can enhance the ability of adriamycin and certain other chemotherapeutic drugs to kill endothelial cells that express CD36 have also been reported to induce apoptosis of tumor cells expressing the CD36 receptor, but not of cells lacking this receptor.

The ability of the Txr1/TSP-1 pathway to modulate taxane sensitivity in prostate cancer cells growing in culture indicates a direct effect on the tumor cells rather than one mediated through angiogenesis. However, we show that the effects of TSP-1 on taxane-induced apoptosis are mediated through a different cell surface receptor, CD47, which previously has been implicated in the effects of TSP-1 and 4N1K on the signaling of platelet activation, cell migration and adhension, phagocytosis, and T-cell activation. The absence CD36 on the surface of M2182 cells and their derivatives, the ability of the CD47-specific 4N1K peptide to recapitulate TSP-1 effects in these cells, the ability of anti-CD47 antibody to mitigate the effects of TSP-1 and the 4N1K peptide on taxol sensitivity, and the ability of pertussis toxin—which interferes with Gi-dependent CD47-mediated cell death—to alter taxane lethality collectively provide convincing evidence of the involvement of CD47 in the modulation of taxol sensitivity by Txr-1 and TSP-1.

The absence of any detectable effect of ABT-510 on taxane sensitivity of M2182 or clone 18 cells is consistent with the absence of CD36 expression on the surface. However, adventitious expression of CD36 in M2182tTA cells failed to sensitize these prostate cancer cells to either the pro-apoptotic effects of ABT510 or to adriamycin (our unpublished data), suggesting that additional functions lacking in the tumor cells we have studied may be required to accomplish CD36-mediated signaling.

IV. Conclusion

Using transcripts initiated at a chromosomally integrated retrovirus-based promoter to perturb gene expression randomly in human prostate cancer cells, we isolated cell clones showing resistance to taxane lethality. We report here the role of a previously unidentified gene, txr1, in this phenotype. We show that txr1 is a transcriptional downregulator of thrombospondin-1 (TSP-1)—known earlier for its anti-angiogenic actions—and that decreased TSP-1 abundance impedes taxane-induced apoptosis in tumor cells. Adventitious downregulation of Txr1 or addition of TSP-1 or mimetic peptide sensitized cells to taxane cytotoxicity by activating signalling through the CD47 receptor (a.k.a. integrin associated protein), whereas interference with CD47 function reduced taxane cytotoxicity. Expression of Txr1 and TSP-1 were correlated negatively with each other and postively with taxol resistance in 13 of 19 NCI-60 cancer cell lines. Our results, which reveal a mechanism that concomitantly regulates both TSP-1 production and taxane resistance, show that the Txr1/TSP-1 pathway is a chemotherapeutic target.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of administering a taxane to a subject in need thereof, said method comprising:
administering to said subject said taxane in conjunction with an effective amount of a nucleic acid TXR1 antagonist, wherein the nucleic acid TXR1 antagonist selectively inhibits expression of a TXR1 nucleic acid that encodes human TXR1 having the sequence of accession number NP_001005355 or NP_001005354, wherein the nucleic acid TXR1 antagonist is a TXR1-specific siRNA.

2. The method according to claim 1, wherein said taxane and said nucleic acid TXR1 antagonist are administered at the same time.

3. The method according to claim 2, wherein said taxane and said nucleic acid TXR1 antagonist are administered as separate formulations.

4. The method according to claim 2, wherein said taxane and said nucleic acid TXR1 antagonist are administered in a single formulation.

5. The method according to claim 1, wherein said taxane and said nucleic acid TXR1 antagonist are administered sequentially.

6. The method according to claim 5, wherein said taxane is administered prior to said nucleic acid TXR1 antagonist.

7. The method according to claim 5, wherein said taxane is administered after said nucleic acid TXR1 antagonist.

8. The method according to claim 1, wherein said taxane is paclitaxel.

9. A method of treating a subject suffering from a cellular proliferative disease condition, said method comprising:
administering to said subject an effective amount of a taxane in conjunction with an effective amount of a nucleic acid TXR1 antagonist to treat said subject for said cellular proliferative disease condition, wherein the nucleic acid TXR1 antagonist selectively inhibits expression of a TXR1 nucleic acid that encodes human TXR1 having the sequence of accession number NP_001005355 or NP_001005354, wherein the nucleic acid TXR1 antagonist is a TXR1-specific siRNA.

10. The method of claim 1, wherein the siRNA is SI1 or SI2.

11. The method of claim 9, wherein the siRNA is SI1 or SI2.

12. The method of claim 1, wherein the subject is in vitro.

* * * * *